(12) United States Patent
Fukuzawa et al.

(10) Patent No.: US 12,030,049 B2
(45) Date of Patent: Jul. 9, 2024

(54) REACTION PROCESSING APPARATUS

(71) Applicant: Go!Foton, Inc., Tsukuba (JP)

(72) Inventors: Takashi Fukuzawa, Tokyo (JP); Osamu Kawaguchi, Tokyo (JP); Hidemitsu Takeuchi, Tokyo (JP)

(73) Assignee: Go!Foton, Inc., Tsukuba (JP)

( * ) Notice: Subject to any disclaimer, the term of this patent is extended or adjusted under 35 U.S.C. 154(b) by 1012 days.

(21) Appl. No.: 16/928,938

(22) Filed: Jul. 14, 2020

(65) Prior Publication Data

US 2020/0398276 A1    Dec. 24, 2020

Related U.S. Application Data

(63) Continuation of application No. PCT/JP2019/000743, filed on Jan. 11, 2019.

(30) Foreign Application Priority Data

Jan. 15, 2018 (JP) .................................. 2018-004295

(51) Int. Cl.
*B01L 3/00*  (2006.01)
*B01L 7/00*  (2006.01)

(52) U.S. Cl.
CPC ... *B01L 3/502738* (2013.01); *B01L 3/502723* (2013.01); *B01L 3/50273* (2013.01);
(Continued)

(58) Field of Classification Search
None
See application file for complete search history.

(56) References Cited

U.S. PATENT DOCUMENTS 6,455,003 B1 *  9/2002  Anvia ...................... G01N 1/40
                                                    436/178
6,656,738 B1 * 12/2003  Vogel ...................... G01N 1/40
                                                    422/89
(Continued)

FOREIGN PATENT DOCUMENTS

CN      101680013 A      3/2010
CN      102286358 A     12/2011
(Continued)

OTHER PUBLICATIONS

Communication dated Feb. 4, 2020, from the Japanese Patent Office in application No. 2019-564763.
(Continued)

*Primary Examiner* — Brian R Gordon
(74) *Attorney, Agent, or Firm* — Sughrue Mion, PLLC

(57) ABSTRACT

A reaction processing apparatus includes: a reaction processing vessel; a temperature control system; and a liquid feeding system. The liquid feeding system includes: a pump having a discharge port; a first air channel; a second air channel; a first three-way valve capable of being switched between a state in which a first air communication port communicates with the discharge port and a state in which the first air communication port is opened to the atmospheric pressure; a second three-way valve capable of being switched between a state in which a second air communication port communicates with the discharge port and a state in which the second air communication port is opened to the atmospheric pressure; and a CPU that controls these components.

10 Claims, 14 Drawing Sheets

Specification includes a Sequence Listing.

(52) U.S. Cl.
CPC ....... B01L 7/525 (2013.01); *B01L 2200/0684* (2013.01); *B01L 2300/048* (2013.01); *B01L 2300/0654* (2013.01); *B01L 2300/0681* (2013.01); *B01L 2300/0867* (2013.01); *B01L 2300/0883* (2013.01); *B01L 2300/14* (2013.01); *B01L 2300/1822* (2013.01); *B01L 2300/1827* (2013.01); *B01L 2400/0487* (2013.01); *B01L 2400/0622* (2013.01); *B01L 2400/0666* (2013.01); *B01L 2400/0694* (2013.01)

(56) References Cited

U.S. PATENT DOCUMENTS

| | | | | |
|---|---|---|---|---|
| 8,888,980 | B2* | 11/2014 | Shiraki | G01N 27/44713 204/601 |
| 10,712,253 | B2* | 7/2020 | Su | G01N 15/0806 |
| 2003/0078751 | A1* | 4/2003 | Juhasz | F04B 51/00 700/285 |
| 2005/0148091 | A1* | 7/2005 | Kitaguchi | B01L 3/523 422/562 |
| 2007/0062583 | A1* | 3/2007 | Cox | G01N 27/44769 73/864.22 |
| 2008/0200343 | A1* | 8/2008 | Clemens | G01N 27/27 506/13 |
| 2011/0045599 | A1* | 2/2011 | Erickson | F04B 49/106 422/68.1 |
| 2012/0077262 | A1* | 3/2012 | Takei | C12Q 1/686 435/289.1 |
| 2012/0156800 | A1* | 6/2012 | Aoki | G01N 21/553 436/180 |
| 2014/0011707 | A1* | 1/2014 | Ye | B01L 3/5027 506/16 |
| 2018/0080570 | A1* | 3/2018 | Block, III | C12M 23/16 |
| 2018/0147573 | A1* | 5/2018 | Hiddessen | B01F 33/813 |
| 2018/0311673 | A1* | 11/2018 | Fukuzawa | B01L 3/502746 |
| 2018/0356434 | A1* | 12/2018 | Gumbrecht | B01L 3/502715 |
| 2019/0168221 | A1* | 6/2019 | Sollier | G01N 1/10 |
| 2020/0086312 | A1* | 3/2020 | Hiddessen | B01L 3/50273 |
| 2021/0170390 | A1* | 6/2021 | Egli | B01L 3/021 |
| 2022/0097045 | A1* | 3/2022 | Masquelier | B01L 3/50273 |

FOREIGN PATENT DOCUMENTS

| | | |
|---|---|---|
| CN | 102899238 A | 1/2013 |
| CN | 107475074 A | 12/2017 |
| JP | 2009-232700 A | 10/2009 |
| JP | 2014-163713 A | 9/2014 |
| JP | 2014-212705 A | 11/2014 |
| WO | 2013/132645 A1 | 9/2013 |
| WO | 2017/094674 A1 | 6/2017 |
| WO | 2017/119382 A1 | 7/2017 |
| WO | 2017/199933 A1 | 11/2017 |
| WO | 2018/084017 A1 | 5/2018 |
| WO | 2018/235766 A1 | 12/2018 |

OTHER PUBLICATIONS

International Search Report dated Apr. 16, 2019, in Application No. PCT/JP2019/000743.
International Preliminary Report on Patentability with translation on Written Opinion dated Jul. 21, 2020, in International Application No. PCT/JP2019/000743.
Notification of Reasons for Refusal dated Feb. 14, 2023 from the Japanese Patent Office in application No. 2020-073337.
Office Action dated Feb. 24, 2023 from the Chinese Patent Office in Application No. 201980008476.0.
Extended European Search Report dated Sep. 3, 2021 from the European Patent Office in EP Application No. 19738743.4.
Office Action dated Sep. 16, 2021 from the Indonesian Intellectual Property Office in Indonesian Application No. P00202005560.
Communication dated May 13, 2022 from the Indian Patent Office in Indian Application No. 202017028970.
Office Action dated Sep. 27, 2022 in JP Application No. 2020-073337.
Office Action dated Jul. 11, 2023 in Israeli Application No. 275802.
Klemm R. et al, "Magnetic particle-based sample-prep and valveing in microfluidic devices", Microfluidics, BioMEMS, and Medical Microsystems X, Feb. 14, 2021, vol. 8251, p. 825108 (Abstract).
Communication dated Nov. 16, 2021, issued in Russian Application No. 2020127018.
Chinese Office Action dated Sep. 25, 2023 in Application No. 201980008476.0.

* cited by examiner

FIG.6

| STEP | MOVEMENT OF SAMPLE | PUMP | FIRST THREE-WAY VALVE | SECOND THREE-WAY VALVE |
|---|---|---|---|---|
| 1 | | OFF | A-C | B-C |
| 2 | LOW TEMPERATURE REGION → HIGH TEMPERATURE REGION | ON | A-C | B-C |
| 3 | REACHED HIGH TEMPERATURE REGION | OFF | A-C | B-C |
| 4 | ON STANDBY IN HIGH TEMPERATURE REGION | OFF | A-C OR B-C | A-C OR B-C |
| 5 | | OFF | B-C | A-C |
| 6 | HIGH TEMPERATURE REGION → LOW TEMPERATURE REGION | ON | B-C | A-C |
| 7 | REACHED LOW TEMPERATURE REGION | OFF | B-C | A-C |
| 8 | ON STANDBY IN LOW TEMPERATURE REGION | OFF | A-C OR B-C | A-C OR B-C |
| | TO STEP 1 | | | |

FIG.7

| STEP | MOVEMENT OF SAMPLE | PUMP | FIRST THREE-WAY VALVE | SECOND THREE-WAY VALVE |
|---|---|---|---|---|
| 1 | LOW TEMPERATURE REGION → HIGH TEMPERATURE REGION | ON | B-C | B-C |
| 2 | | ON | A-C | B-C |
| 3 | REACHED HIGH TEMPERATURE REGION | ON | B-C | B-C |
| 4 | ON STANDBY IN HIGH TEMPERATURE REGION | OFF | A-C OR B-C | A-C OR B-C |
| 5 | HIGH TEMPERATURE REGION → LOW TEMPERATURE REGION | ON | B-C | B-C |
| 6 | | ON | B-C | A-C |
| 7 | REACHED LOW TEMPERATURE REGION | ON | B-C | B-C |
| 8 | ON STANDBY IN LOW TEMPERATURE REGION | OFF | A-C OR B-C | A-C OR B-C |
| | TO STEP 1 | | | |

FIG.11

| STEP | MOVEMENT OF SAMPLE | PUMP | FIRST THREE-WAY VALVE | SECOND THREE-WAY VALVE |
|---|---|---|---|---|
| 1 | | OFF | A-C | B-C |
| 2 | LOW TEMPERATURE REGION → HIGH TEMPERATURE REGION | ON | A-C | B-C |
| 3 | REACHED HIGH TEMPERATURE REGION | OFF | A-C | B-C |
| 4 | ON STANDBY IN HIGH TEMPERATURE REGION | OFF | BOTH A-C OR BOTH B-C | BOTH A-C OR BOTH B-C |
| 5 | | OFF | B-C | A-C |
| 6 | HIGH TEMPERATURE REGION → LOW TEMPERATURE REGION | ON | B-C | A-C |
| 7 | REACHED LOW TEMPERATURE REGION | OFF | B-C | A-C |
| 8 | ON STANDBY IN LOW TEMPERATURE REGION | OFF | BOTH A-C OR BOTH B-C | BOTH A-C OR BOTH B-C |
| | TO STEP 1 | | | |

FIG.13

| STEP | MOVEMENT OF SAMPLE | PUMP | FIRST THREE-WAY VALVE | SECOND THREE-WAY VALVE | SOLENOID VALVE |
|---|---|---|---|---|---|
| 1 | PRESSURIZATION | OFF | A-C | B-C | OPEN |
| 2 | LOW TEMPERATURE REGION → HIGH TEMPERATURE REGION | OFF | A-C | B-C | CLOSED |
| 3 |  | ON | A-C | B-C | CLOSED |
| 4 | REACHED HIGH TEMPERATURE REGION | OFF | A-C | B-C | CLOSED |
| 5 | ON STANDBY IN HIGH TEMPERATURE REGION | OFF | BOTH A-C OR BOTH B-C | BOTH B-C | OPEN |
| 6 | HIGH TEMPERATURE REGION → LOW TEMPERATURE REGION | OFF | B-C | A-C | CLOSED |
| 7 |  | ON | B-C | A-C | CLOSED |
| 8 | REACHED LOW TEMPERATURE REGION | OFF | B-C | A-C | CLOSED |
| 9 | ON STANDBY IN LOW TEMPERATURE REGION | OFF | BOTH A-C OR BOTH B-C | BOTH B-C | OPEN |
|  | TO STEP 2 |  |  |  |  |

FIG.14

| STEP | MOVEMENT OF SAMPLE | PUMP | FIRST THREE-WAY VALVE | SECOND THREE-WAY VALVE | SOLENOID VALVE |
|---|---|---|---|---|---|
| 1 | PRESSURIZATION | OFF | A-C | B-C | OPEN |
| 2 | LOW TEMPERATURE REGION → HIGH TEMPERATURE REGION | OFF | A-C | B-C | CLOSED |
| 3 | REACHED HIGH TEMPERATURE REGION | ON | A-C | B-C | CLOSED |
| 4 | ON STANDBY IN HIGH TEMPERATURE REGION | OFF | A-C | B-C | CLOSED |
| 5 | | OFF | BOTH A-C OR BOTH B-C | A-C | CLOSED |
| 6 | HIGH TEMPERATURE REGION → LOW TEMPERATURE REGION | OFF | B-C | A-C | CLOSED |
| 7 | REACHED LOW TEMPERATURE REGION | ON | B-C | A-C | CLOSED |
| 8 | ON STANDBY IN LOW TEMPERATURE REGION | OFF | B-C | A-C | CLOSED |
| 9 | | OFF | BOTH A-C OR BOTH B-C | | CLOSED |
| | TO STEP 2 | | | | |

REACTION PROCESSING APPARATUS

BACKGROUND OF THE INVENTION

1. Field of the Invention

The present invention relates to reaction processing apparatuses used for polymerase chain reactions (PCR).

2. Background Art

Genetic testing is widely used for examinations in a wide variety of medical fields, identification of farm products and pathogenic microorganisms, safety assessment for food products, and even for examinations for pathogenic viruses and a variety of infectious diseases. In order to detect with high sensitivity a minute amount of DNA, methods of analyzing the resultant obtained by amplifying a portion of DNA are known. Above all, a method that uses PCR is a remarkable technology where a certain portion of a very small amount of DNA collected from an organism or the like is selectively amplified.

In PCR, a predetermined thermal cycle is applied to a sample in which a biological sample containing DNA and a PCR reagent consisting of primers, enzymes, and the like are mixed so as to cause denaturation, annealing, and elongation reactions to be repeated so that a specific portion of DNA is selectively amplified.

It is a common practice to perform PCR by putting a predetermined amount of a target sample into a PCR tube or a reaction processing vessel such as a microplate (microwell) in which a plurality of holes are formed. However, in recent years, PCR using a reaction processing vessel (also referred to as "chip") provided with a micro-channel that is formed on a substrate is practiced (e.g. Patent Document 1).

[Patent Document 1] Japanese Patent Application Publication No. 2009-232700

SUMMARY OF THE INVENTION

When performing PCR using a reaction processing vessel provided with a channel, a thermal cycle is applied to the sample by setting temperature regions such as a high temperature region and a low temperature region in the channel and moving the sample in a reciprocating manner inside the channel.

As a method of reciprocating a sample inside a channel of a reaction processing vessel, a method using two liquid feeding mechanisms can be considered. The liquid feeding mechanisms are, for example, pumps or the like. A pump is connected to each end of the channel, and the sample is moved by adjusting the pressure inside the channel.

However, there may be individual differences in the characteristics of these pumps. In a method using two or more pumps, there is a problem that it is difficult to accurately control the pressure inside the channel when there are individual differences in the characteristics of these pumps.

In this background, a purpose of the present invention is to provide a reaction processing apparatus that can easily control the movement of a sample inside a channel of a reaction processing vessel.

A reaction processing apparatus according to one embodiment of the present invention includes: a reaction processing vessel including a channel in which a sample moves and a pair composed of a first air communication port and a second air communication port that are provided at respective ends of the channel; a temperature control unit that provides a first temperature region maintained at a first temperature and a second temperature region maintained at a second temperature higher than the first temperature between the first air communication port and the second air communication port in the channel; and a liquid feeding system that moves and stops the sample in the channel. The liquid feeding system includes: a pump capable of discharging air from a discharge port; a first air channel that connects the discharge port of the pump and the first air communication port of the react ion processing vessel; a second air channel that connects the discharge port of the pump and the second air communication port of the reaction processing vessel; a first switching valve that is arranged in the first air channel and is capable of being switched between a state in which the first air communication port communicates with the discharge port and a state in which the first air communication port is opened to the atmospheric pressure; a second switching valve that is arranged in the second air channel and is capable of being switched between a state in which the second air communication port communicates with the discharge port and a state in which the second air communication port is opened to the atmospheric pressure; and a control unit that controls the operation of the pump, the operation of the first switching valve, and the operation of the second switching valve.

The first temperature region may be located on the first air communication port side, and the second temperature region may be located on the second air communication port side. The control unit may be configured to: discharge air from the pump and change the first switching valve to be in the state in which the first air communication port communicates with the discharge port and the second switching valve to be in the state in which the second air communication port is opened to the atmospheric pressure, when a sample is moved from the first temperature region to the second temperature region; and discharge air from the pump and change the first switching valve to be in the state in which the first air communication port is opened to the atmospheric pressure and the second switching valve to be in the state in which the second air communication port communicates with the discharge port, when the sample is moved from the second temperature region to the first temperature region.

The control unit may stop the discharging of the air from the pump when stopping the sample inside the channel.

Pressure on the primary side and pressure on the secondary side may become equal in the pump when the pump is stopped. When stopping the sample inside the channel, the control unit may change the first switching valve to be in the state in which the first air communication port is opened to the atmospheric pressure and the second switching valve to be in the state in which the second air communication port is opened to the atmospheric pressure.

The first switching valve and the second switching valve may be three-way valves.

Another embodiment of the present invention also relates to a reaction processing apparatus. This apparatus includes: a reaction processing vessel including a channel in which a sample moves and a pair composed of a first air communication port and a second air communication port that are provided at respective ends of the channel; a temperature control unit that provides a first temperature region maintained at a first temperature and a second temperature region maintained at a second temperature higher than the first temperature between the first air communication port and the second air communication port in the channel; and a liquid feeding system that moves and stops the sample in the channel. The liquid feeding system includes: a pressurizing chamber that has an internal pressure maintained to be higher than the atmospheric pressure in the surrounding environment of the reaction processing apparatus; a pump that is arranged inside the pressurizing chamber and is capable of discharging air from a discharge port; a first air channel that connects the discharge port of the pump and the first air communication port of the reaction processing vessel; a second air channel that connects the discharge port of the pump and the second air communication port of the reaction processing vessel; a first switching valve that is arranged in the first air channel and is capable of being switched between a state in which the first air communication port communicates with the discharge port and a state in which the first air communication port is opened to an internal space of the pressurizing chamber; a second switching valve that is arranged in the second air channel and is capable of being switched between a state in which the second air communication port communicates with the discharge port and a state in which the second air communication port is opened to the internal space of the pressurizing chamber; and a control unit that controls the operation of the pump, the operation of the first switching valve, and the operation of the second switching valve.

The first temperature region may be located on the first air communication port side, and the second temperature region may be located on the second air communication port side. The control unit may be configured to: discharge air from the pump and change the first switching valve to be in the state in which the first air communication port communicates with the discharge port and the second switching valve to be in the state in which the second air communication port is opened to the internal space of the pressurizing chamber, when a sample is moved from the first temperature region to the second temperature region; and discharge air from the pump and change the first switching valve to be in the state in which the first air communication port is opened to the internal space of the pressurizing chamber and the second switching valve to be in the state in which the second air communication port communicates with the discharge port, when the sample is moved from the second temperature region to the first temperature region.

The control unit may stop the discharging of the air from the pump when stopping the sample inside the channel.

Pressure on the primary side and pressure on the secondary side may become equal in the pump when the pump is stopped. When stopping the sample inside the channel, the control unit may change the first switching valve to be in the state in which the first air communication port is opened to the internal space of the pressurizing chamber and the second switching valve to be in the state in which the second air communication port is opened to the internal space of the pressurizing chamber.

The first switching valve and the second switching valve may be three-way valves.

BRIEF DESCRIPTION OF THE DRAWINGS

Embodiments will now be described, by way of example only, with reference to the accompanying drawings which are meant to be exemplary, not limiting, and wherein like elements are numbered alike in several FIGS., in which:

FIG. 6 is a diagram for explaining a method of controlling a pump, a first three-way valve, and a second three-way valve in the reaction processing apparatus shown in FIG. 5;

FIG. 7 is a diagram for explaining another method of controlling the pump, the first three-way valve, and the second three-way valve in the reaction processing apparatus shown in FIG. 5;

FIG. 11 is a diagram for explaining another method of controlling a pump, a first three-way valve, and a second three-way valve in the reaction processing apparatus shown in FIG. 10;

FIG. 13 is a diagram for explaining a method of controlling a pump, a first three-way valve, a second three-way valve, and a solenoid valve in the reaction processing apparatus shown in FIG. 12; and FIG. 14 is a diagram for explaining another method of controlling the pump, the first three-way valve, the second three-way valve, and the solenoid valve in the reaction processing apparatus shown in FIG. 12.

DETAILED DESCRIPTION OF THE INVENTION

Figures 1A, 1B:
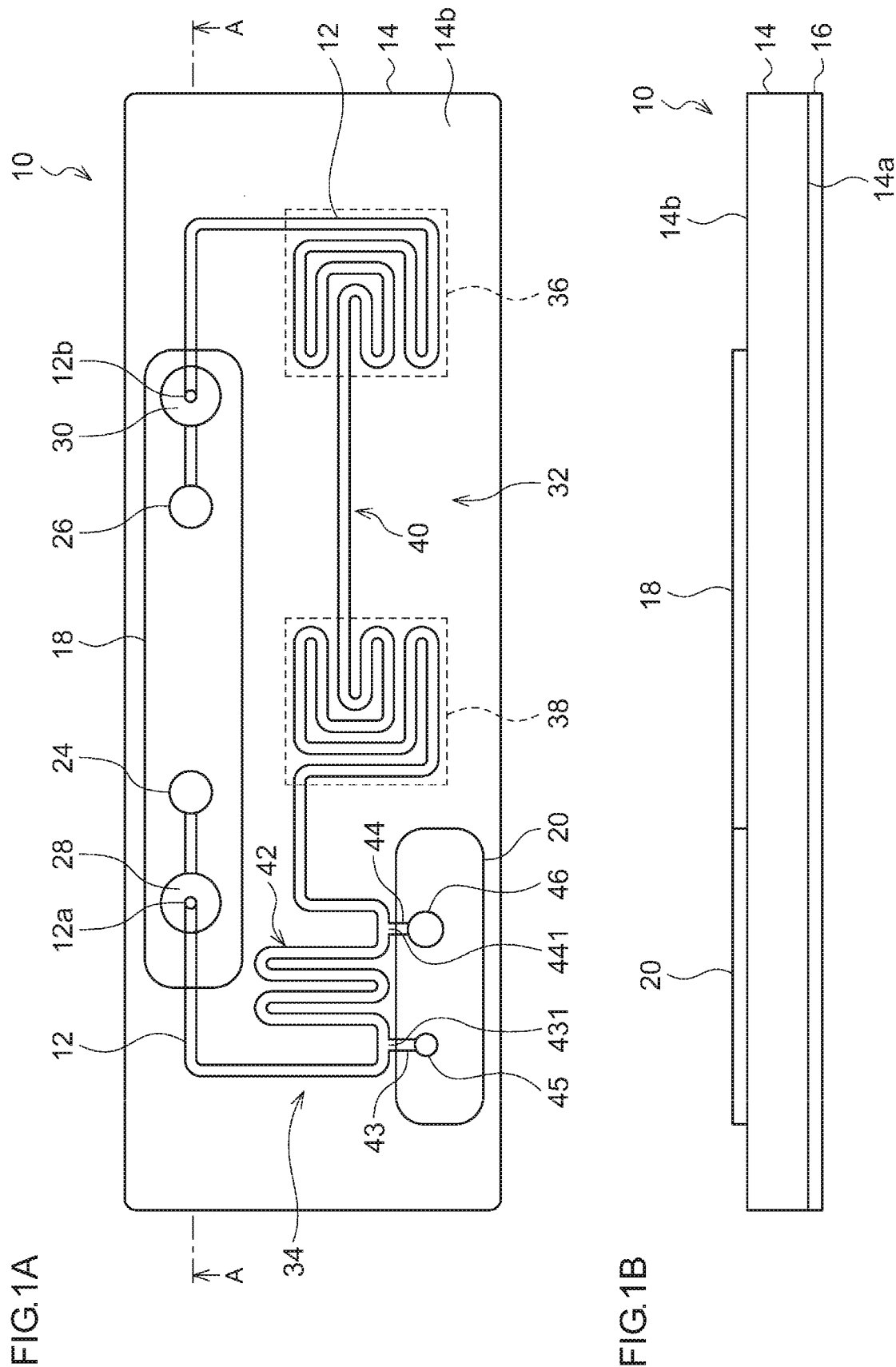
FIGS. 1A and 1B are diagrams for explaining a reaction processing vessel usable in a reaction processing apparatus according to an embodiment of the present invention.

An explanation will be given in the following regarding a reaction processing apparatus according to an embodiment of the present invention. The same or equivalent constituting elements, members, and processes illustrated in each drawing shall be denoted by the same reference numerals, and duplicative explanations will be omitted appropriately. Further, the embodiments do not limit the invention and are shown for illustrative purposes, and not all the features described in the embodiments and combinations thereof are necessarily essential to the invention.

Figure 2:
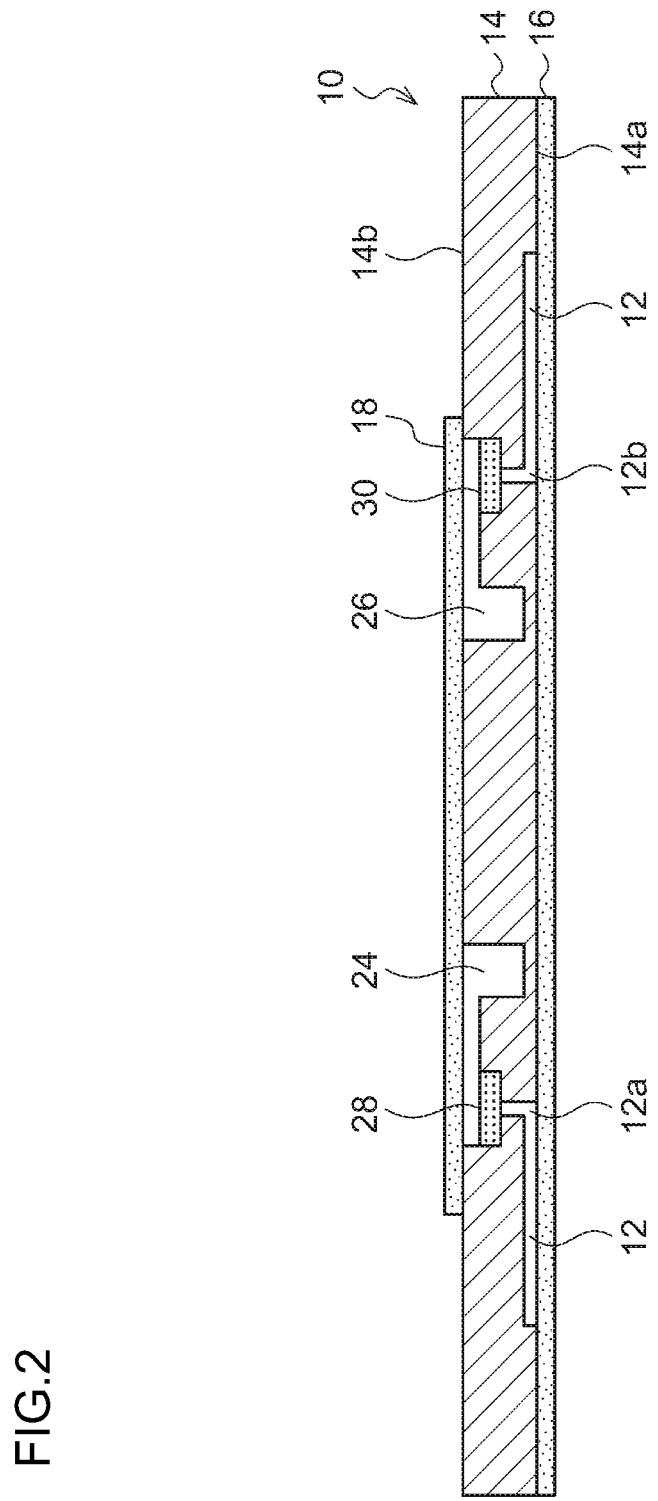
FIG. 2 is a cross-sectional view of the reaction processing vessel shown in FIG. 1A that is sectioned along line A-A.
Figure 3:
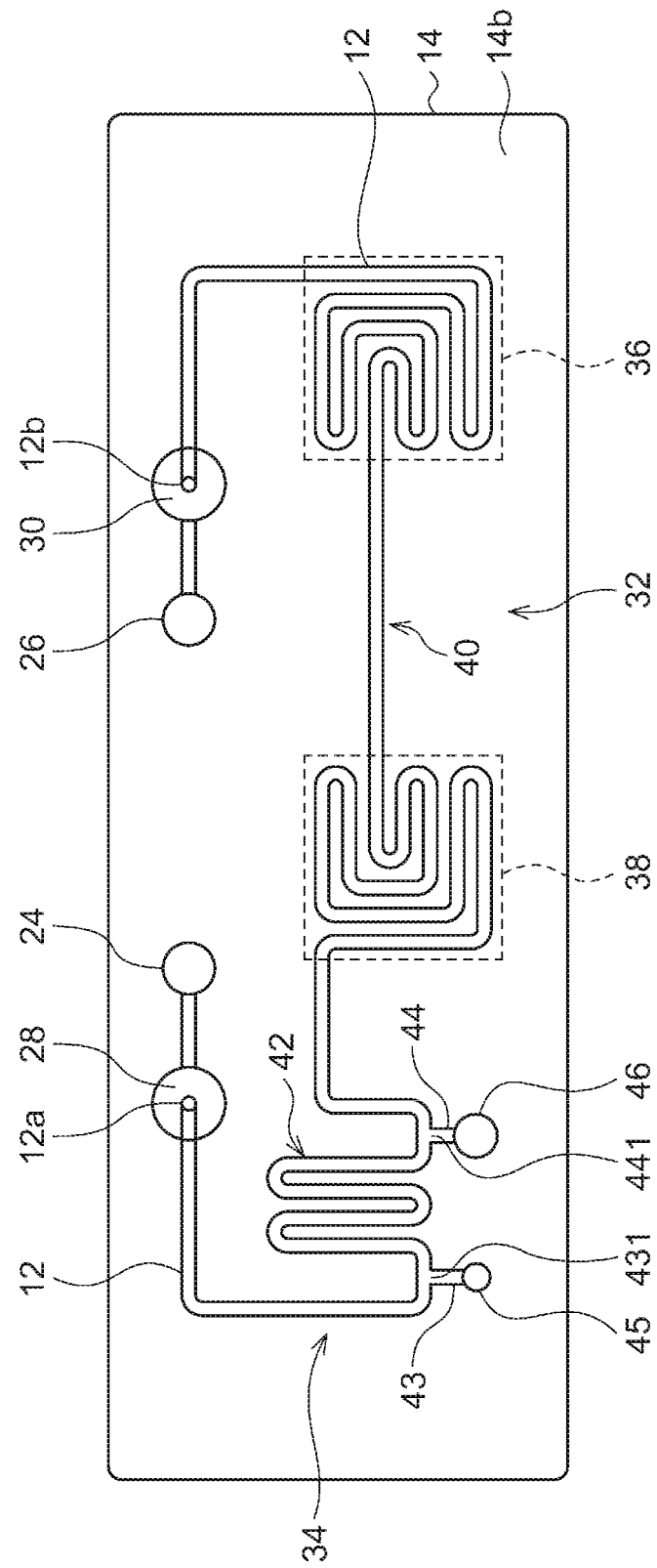
FIG. 3 is a plan view of a substrate provided in the reaction processing vessel.

FIGS. 1A and 1B are diagrams for explaining a reaction processing vessel 10 usable in a reaction processing apparatus according to an embodiment of the present invention. FIG. 1A is a plan view of the reaction processing vessel 10, and FIG. 1B is a front view of the reaction processing vessel 10. FIG. 2 is a cross-sectional view of the reaction processing vessel 10 shown in FIG. 1A that is sectioned along line A-A. FIG. 3 is a plan view of a substrate 14 provided in the reaction processing vessel 10.

The reaction processing vessel 10 comprises a resinous substrate 14 having a groove-like channel 12 formed on a lower surface 14a thereof, a channel sealing film 16, which is attached on the lower surface 14a of the substrate 14, for sealing the channel 12, and two sealing films (a first sealing film 18 and a second sealing film 20) attached on an upper surface 14b of the substrate 14.

The substrate 14 is preferably formed of a material that is stable under temperature changes and is resistant to a sample solution that is used. Further, the substrate 14 is preferably formed of a material that has good moldability, a good transparency and barrier property, and a low self-fluorescent property. As such a material, an inorganic material such as glass, silicon (Si), or the like, a resin such as acrylic, polyester, silicone, or the like, and particularly a cycloolefin polymer resin (COP) are preferred. An example of the dimensions of the substrate 14 includes a long side of 76 mm, a short side of 26 mm, and a thickness of 4 mm.

The groove-like channel 12 is formed on the lower surface 14a of the substrate 14. In the reaction processing vessel 10, most of the channel 12 is formed in the shape of a groove exposed on the lower surface 14a of the substrate 14. This is for allowing for easy molding by injection molding using a metal mold or the like. In order to seal this groove so as to make use of the groove as a channel, the channel sealing film 16 is attached on the lower surface 14a of the substrate 14. An example of the dimensions of the channel 12 includes a width of 0.7 mm and a depth of 0.7 mm.

The channel sealing film 16 may be sticky on one of the main surfaces thereof or may have a functional layer that exhibits stickiness or adhesiveness through pressing, energy irradiation with ultraviolet rays or the like, heating, etc., formed on one of the main surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive, that has a low self-fluorescent property. In this respect, a transparent film made of a resin such as a cycloolefin polymer, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the reaction processing vessel 10.

A first air communication port 24 is formed at the position of one end 12a of the channel 12 in the substrate 14. A second air communication port 26 is formed at the position of the other end 12b of the channel 12 in the substrate 14. The pair, the first air communication port 24 and the second air communication port 26, is formed so as to be exposed on the upper surface 14b of the substrate 14.

A first filter 28 is provided between the first air communication port 24 and one end 12a of the channel 12 in the substrate 14. A second filter 30 is provided between the second air communication port 26 and the other end 12b of the channel 12 in the substrate 14. The pair, the first filter 28 and the second filter 30, provided at respective ends of the channel 12, has good low impurity characteristics and also allows only air to pass therethrough so as to prevent contamination such that the amplification of target DNA and the detection of the target DNA are not interrupted. As a filter material, for example, a material obtained by subjecting polyethylene to a water repellent treatment can be used. Alternatively, a known material can be selected as long as the material has the above function. Regarding the dimensions of the first filter 28 and the second filter 30, the first filter 28 and the second filter 30 are formed so as to fit without any gap in a filter installation space formed in the substrate 14 and may have, for example, a diameter of 4 mm and a thickness of 2 mm.

As shown in FIG. 1A, between the pair consisting of the first air communication port 24 and the second air communication port 26, the channel 12 includes a thermal cycle region 32 for applying a thermal cycle to the sample and a dispensing region 34 for performing so-called dispensing where a predetermined amount of the sample is extracted. The thermal cycle region 32 is located on the side of the second air communication port 26 in the channel 12. The dispensing region 34 is located on the side of the first air communication port 24 in the channel 12. The thermal cycle region 32 and the dispensing region 34 communicate with each other. By moving the sample dispensed in the dispensing region 34 to the thermal cycle region 32 such that the sample continuously reciprocates between reaction regions maintained at a predetermined temperature that are included in the thermal cycle region 32, a thermal cycle can be applied to the sample.

When the reaction processing vessel 10 is mounted on a reaction processing apparatus described later, the thermal cycle region 32 of the channel 12 includes a reaction region (hereinafter referred to as "low temperature region 38") maintained at a relatively low temperature (about 60° C.), a reaction region (hereinafter referred to as "high temperature region 36") maintained at a higher temperature (about 95° C.), and a connection region 40 connecting the high temperature region 36 and the low temperature region 38. The low temperature region 38 is located on the side of the first air communication port 24 (in other words, on the dispensing region 34 side), and the high temperature region 36 is located on the side of the second air communication port 26.

The high temperature region 36 and the low temperature region 38 each include a serpiginous shape channel where a turn is continuously made by combining curved portions and straight portions. In a case where a serpiginous shape channel is used as described above, an effective area that is limited such as that of a heater or the like constituting a temperature control means described later can be effectively used, and there are advantages that temperature variance in the reaction region is easily reduced and that the substantial size of the reaction processing vessel can be reduced, contributing to the downsizing of the reaction processing apparatus. The connection region 40 may be a linear channel.

The dispensing region 34 of the channel 12 is located between the low temperature region 38 in the thermal cycle region 32 and the first filter 28. As described above, the dispensing region 34 has a function of dispensing a predetermined amount of the sample to be subjected to PCR. The dispensing region 34 includes a dispensing channel 42 for defining a predetermined amount of the sample, two branch channels (a first branch channel 43 and a second branch channel 44) branching from the dispensing channel 42, a first sample introduction port 45 arranged at an end of the first branch channel 43, and a second sample introduction port 46 arranged at an end of the second branch channel 44. The first sample introduction port 45 communicates with the dispensing channel 42 via the first branch channel 43. The second sample introduction port 46 communicates with the dispensing channel 42 via the second branch channel 44. The dispensing channel 42 is a serpiginous shape channel in order to dispense a predetermined amount of the sample using a minimum area. The first sample introduction port 45 and the second sample introduction port 46 are formed so as to be exposed on the upper surface 14b of the substrate 14. The first sample introduction port 45 is formed to have a comparatively small diameter, and the second sample introduction port 46 is formed to have a relatively large diameter.

When a branch point at which the first branch channel 43 branches from the dispensing channel 42 is defined as a first branch point 431 and a branch point at which the second branch channel 44 branches from the dispensing channel 42 is defined as a second branch point 441, the volume of the sample to be subjected to PCR is almost determined by the volume inside the dispensing channel 42 between the first branch point 431 and the second branch point 441.

In the reaction processing vessel 10, the dispensing region 34 is provided between the thermal cycle region 32 and the first filter 28. However, the position of the dispensing region 34 is not limited to this, and the dispensing region 34 may be provided between the thermal cycle region 32 and the second filter 30. As long as the dispensing can be done accurately using a pipette or the like, the channels may be formed without providing the dispensing region 34 or formed such that the sample can be introduced directly into the thermal cycle region 32 or the like.

The first air communication port 24, the second air communication port 26, the first filter 28, the second filter 30, the first sample introduction port 45, and the second sample introduction port 46 are exposed on the upper surface 14b of the substrate 14. Therefore, in order to seal the first air communication port 24, the second air communication port 26, the first filter 28, and the second filter 30, the first sealing film 18 is attached to the upper surface 14b of the substrate 14. In order to seal the first sample introduction port 45 and the second sample introduction port 46, the second sealing film 20 is attached to the upper surface 14b of the substrate 14. In a state where the first sealing film 18 and the second sealing film 20 are attached, the entire channel forms a closed space.

The first sealing film 18 that is used has a size that allows the first air communication port 24, the second air communication port 26, the first filter 28, and the second filter 30 to be sealed at the same time. A liquid feeding system (described later) is connected to the first air communication port 24 and the second air communication port 26 by perforating the respective parts of the first sealing film 18 that correspond to the first air communication port 24 and the second air communication port 26 by a hollow needle (syringe needle with a sharp tip) provided in the liquid feeding system. Therefore, the first sealing film 18 is preferably a film made of a material that is easily perforated by the needle and/or have a thickness that is easily perforated by the needle. In the reaction processing vessel 10, the sealing film having a size that is capable of sealing the first air communication port 24, the second air communication port 26, the first filter 28, and the second filter 30 at the same time is described. However, these air communication ports and filters may be sealed separately. Further, the film sealing the first air communication port 24 and the second air communication port 26 may be peeled off so as to be connected to the liquid feeding system.

As the second sealing film 20, a sealing film having a size that is capable of sealing the first sample introduction port 45 and the second sample introduction port 46 is used. Introduction of a sample into the channel 12 through the first sample introduction port 45 and the second sample introduction port 46 is performed by once peeling the second sealing film 20 from the substrate 14, and, after the introduction of a predetermined amount of sample, the second sealing film 20 is put back being attached to the upper surface 14b of the substrate 14 again. Therefore, as the second sealing film 20, a film is desired that is sticky enough to holdup through several cycles of attaching and peeling. Alternatively, as the second sealing film 20, a new film may be attached after the introduction of a sample. In this case, the importance of the property related to repetitive attaching and peeling can be lessened.

In the same way as in the channel sealing film 16, the first sealing film 18 and the second sealing film 20 may have an adhesive layer or a functional layer exhibiting stickiness or adhesiveness by pressing that is formed on one of the main surfaces thereof. As an example, a transparent film made of a resin such as a cycloolefin polymer, polyester, polypropylene, polyethylene or acrylic is suitable but is not limited thereto. As described above, the property such as stickiness or the like desirably do not degrade to such an extent that the use is affected even after attaching and peeling of multiple times. However, in a case where a new film is attached after the peeling and the introduction of a sample or the like or after the connection to a pressure-type pump, the importance of this property related to the attaching and peeling can be lessened.

An explanation will be given next regarding a method of using the reaction processing vessel 10 formed as described above. First, a sample to be amplified through a thermal cycle is prepared. The sample includes, for example, those obtained by adding a thermostable enzyme and four types of deoxyribonucleoside triphosphates (dATP, dCTP, dGTP, dTTP) as PCR reagents. A primer and a fluorescent probe that specifically react to DNA subjected to a reaction process is mixed to this. For these, commercially available real-time PCR reagent kits and the like can be also used. Further, a mixture containing one or two or more types of DNAs to be subjected to the reaction process (for example, to be subjected to amplification by PCR) is added.

Next, the second sealing film 20 is peeled off from the substrate 14 such that the first sample introduction port 45 and the second sample introduction port 46 are open.

Figure 4:
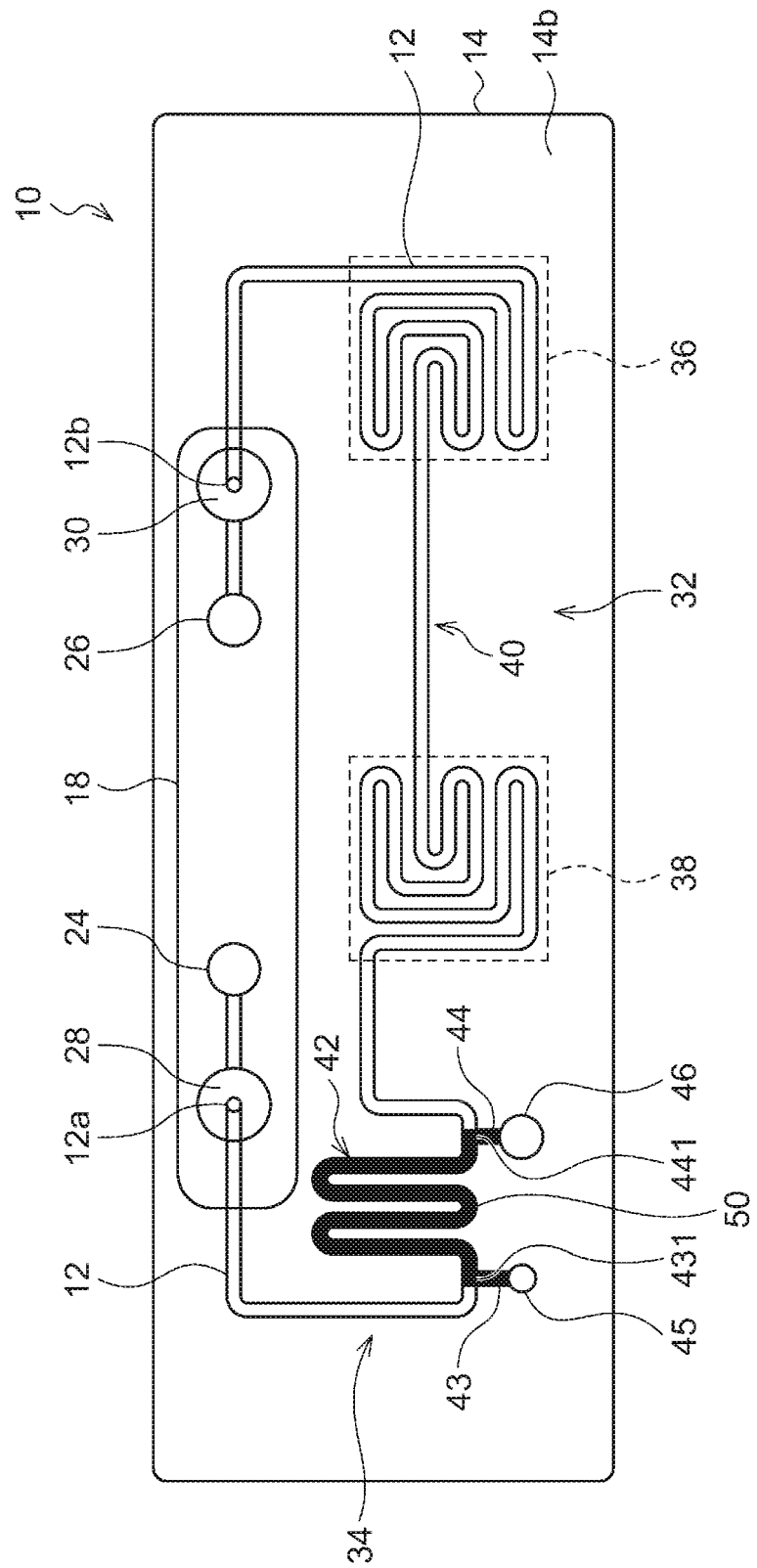
FIG. 4 is a diagram schematically showing a state where a sample is introduced into the reaction processing vessel.

The sample is then introduced to a sample introduction port by a dropper, a syringe, or the like. FIG. 4 schematically shows a state where a sample 50 is introduced into the reaction processing vessel 10. The sample 50 is introduced into the dispensing channel 42 through either one of the first sample introduction port 45 and the sample introduction port 46. The method for the introduction is not limited to this. Alternatively, for example, an appropriate amount of the sample 50 may be directly introduced using a pipette or a dropper. When the sample is introduced using a pipette, the sample 50 is introduced through the first sample introduction port 45, which has a relatively small diameter. In this case, the sample 50 is loaded into the dispensing channel 42 toward the second sample introduction port 46. When the sample 50 is introduced using a dropper, the sample 50 is introduced through the second sample introduction port 46, which has a relatively large diameter. In this case, the sample 50 is loaded into the dispensing channel 42 toward the first sample introduction port 45. The excess portion of the sample introduced through either one of the sample introduction ports that exceeds the volume of the branch channel becomes accumulated at the other one of the sample introduction ports. Therefore, in order to utilize the sample introduction port part as a kind of reservoir, the sample introduction port part may be made to have a certain space. As will be described later, the sample 50 loaded into the dispensing channel 42 between the first branch point 431 and the second branch point 441 undergoes PCR by pressurization from the first air communication port 24 and the second air communication port 26. In this manner, the dispensing region 34 of the reaction processing vessel 10 has a function of dispensing a predetermined amount of sample.

Next, the second sealing film 20 is attached to the substrate 14 again such that the first sample introduction port 45 and the second sample introduction port 46 are sealed. Instead of the second sealing film 20 that has been peeled off, a new second sealing film 20 may be attached. This completes the introduction of the sample 50 into the reaction processing vessel 10.

The above-mentioned dispensing function in the reaction processing vessel is not to prevent introduction of the sample while precisely dispensing the sample with a pipette alone.

Figure 5:
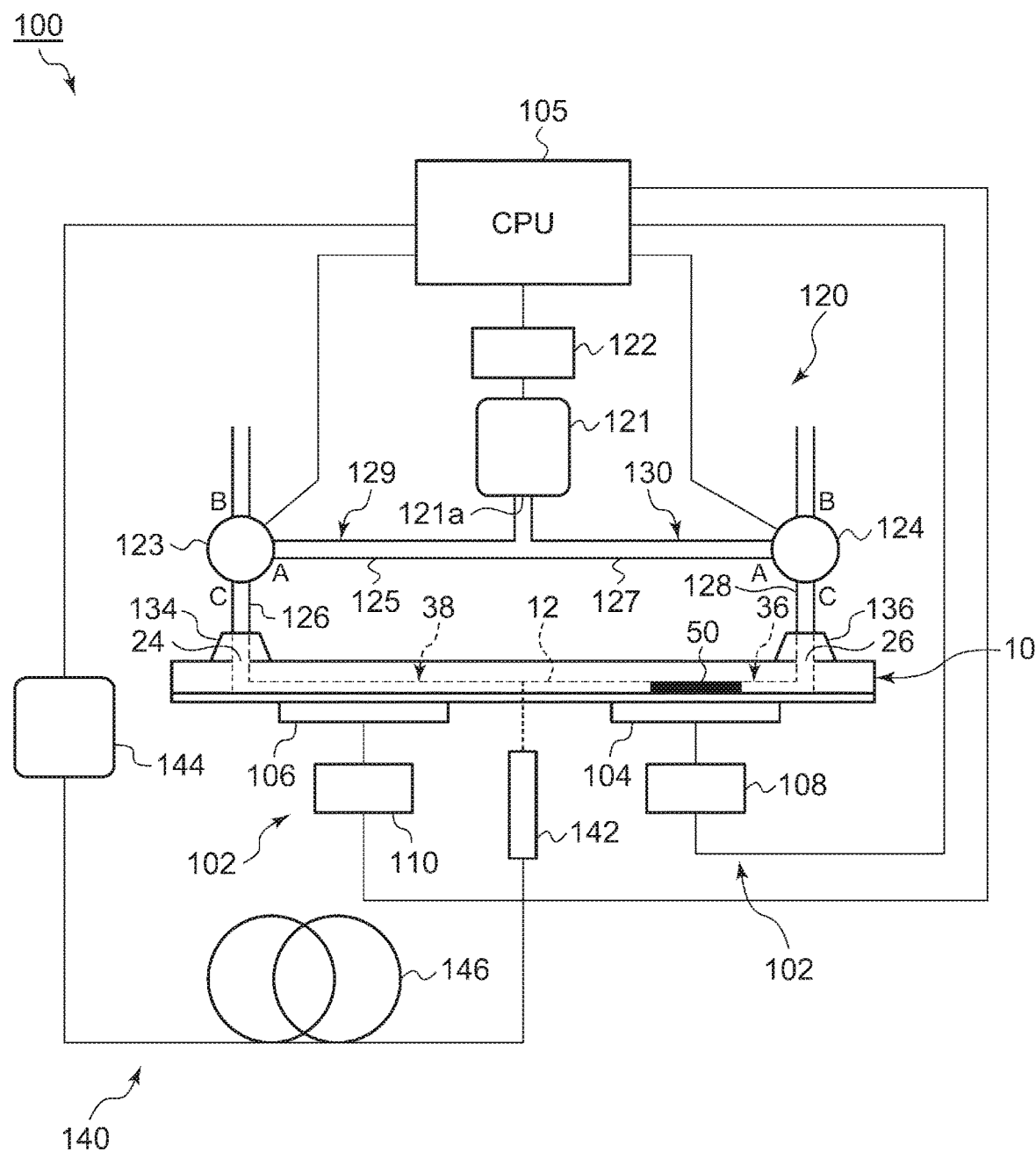
FIG. 5 is a schematic diagram for explaining a reaction processing apparatus according to an embodiment of the present invention.

FIG. 5 is a schematic diagram for explaining a reaction processing apparatus 100 according to the embodiment of the present invention.

The reaction processing apparatus 100 according to the present embodiment includes a vessel installation unit (not shown) in which the reaction processing vessel 10 is installed, a temperature control system 102, and a CPU 105. As shown in FIG. 5, relative to the reaction processing vessel 10 installed in the vessel installation unit, the temperature control system 102 is formed so as to be able to accurately maintain and control the temperature of the high temperature region 36 in the channel 12 of the reaction processing vessel 10 to be about 95° C. and the temperature of the low temperature region 38 to be about 60° C.

The temperature control system 102 is for adjusting the temperature of each temperature region of a thermal cycle region and is specifically provided with a high temperature heater 104 for heating the high temperature region 36 of the channel 12, a low temperature heater 106 for heating the low temperature region 38 of the channel 12, a temperature sensor (not shown) such as, for example, a thermocouple or the like for measuring the actual temperature of each temperature region, a high temperature heater driver 108 for controlling the temperature of the high temperature heater 104, and a low temperature heater driver 110 for controlling the temperature of the low temperature heater 106. Further, the reaction processing apparatus 100 may include a dispensing heater (not shown) for heating the dispensing region of the channel 12 and a dispensing heater driver (not shown). Information on the actual temperature measured by the temperature sensor is sent to the CPU 105. Based on the information on the actual temperature of each temperature region, the CPU 105 controls each heater driver such that the temperature of each heater becomes a predetermined temperature. Each heater may be, for example, a resistance heating element, a Peltier element, or the like. The temperature control system 102 may be further provided with other components for improving the temperature controllability of each temperature region.

The reaction processing apparatus 100 according to the present embodiment is further provided with a fluorescence detector 140. As described above, a predetermined fluorescent probe is added to the sample 50. Since the intensity of a fluorescence signal emitted from the sample 50 increases as the amplification of the DNA proceeds, the intensity value of the fluorescence signal can be used as an index serving as a decision material for the progress of the PCR or the termination of the reaction.

As the fluorescence detector 140, an optical fiber-type fluorescence detector FLE-510 manufactured by Nippon Sheet Glass Co., Ltd., can be used, which is a very compact optical system that allows for rapid measurement and the detection of fluorescence regardless of whether the place is a lighted place or a dark place. This optical fiber-type fluorescence detector allows the wavelength characteristic of the excitation light/fluorescence to be tuned such that the wavelength characteristic is suitable for the characteristic of fluorescence emitted from the sample 50 and thus allows an optimum optical and detection system for a sample having various characteristics to be provided. Further, the optical fiber-type fluorescence detector is suitable for detecting fluorescence from a sample existing in a small or narrow region such as a channel because of the small diameter of a ray of light brought by the optical fiber-type fluorescence detector and is also excellent in response speed.

The optical fiber-type fluorescence detector 140 is provided with an optical head 142, a fluorescence detector driver 144, and an optical fiber 146 connecting the optical head 142 and the fluorescence detector driver 144. The fluorescence detector driver 144 includes a light source for excitation light (LED, a laser, or a light source adjusted to emit other specific wavelengths), an optical fiber-type multiplexer/demultiplexer and a photoelectric conversion device (PD, APD, or a light detector such as a photomultiplier) (neither of which is shown), and the like and formed of a driver or the like for controlling these. The optical head 142 is formed of an optical system such as a lens and has a function of directionally irradiating the sample with excitation light and collecting fluorescence emitted from the sample. The collected fluorescence is separated from the excitation light by the optical fiber-type multiplexer/demultiplexer inside the fluorescence detector driver 144 through the optical fiber 146 and converted into an electric signal by the photoelectric conversion element.

In the reaction processing apparatus 100 according to the present embodiment, the optical head 142 is arranged such that fluorescence from the sample 50 in the channel connecting the high temperature region 36 and the low temperature region 38 can be detected. Since the reaction progresses while the sample 50 is repeatedly moved in a reciprocating manner in the channel such that predetermined DNA contained in the sample 50 is amplified, by monitoring a change in the amount of detected fluorescence, the progress of the DNA amplification can be learned in real time. Further, in the reaction processing apparatus 100 according to the present embodiment, an output value from the fluorescence detector 140 is utilized for controlling the movement of the sample 50. The fluorescence detector is not limited to an optical fiber-type fluorescence detector as long as the fluorescence detector exhibits the function of detecting fluorescence from a sample.

The reaction processing apparatus 100 according to the present embodiment is further provided with a liquid feeding system 120 for moving and stopping the sample 50 inside the channel 12 of the reaction processing vessel 10. The liquid feeding system 120 includes a pump 121, a pump driver 122 for driving the pump 121, a first three-way valve 123, and a second three-way valve 124. The pump driver 122, the first three-way valve 123, and the second three-way valve 124 are controlled by the CPU 105.

The pump 121 can discharge air from a discharge port 121a. The pump 121 may be, for example, a micro blower pump comprising a diaphragm pump. As the pump 121, for example, a micro blower pump (MZB1001 T02 model) manufactured by Murata Manufacturing Co., Ltd., or the like can be used. While this micro blower pump can increase the pressure on a secondary side to be higher than a primary side during operation, the pressure on the primary side and the pressure on the secondary side become equal at the moment when the pump is stopped or when the pump is stopped. The CPU 105 controls the air supply and pressurization from the pump 121 via the pump driver 122.

The discharge port 121a of the pump 121 is connected to the first air communication port 24 of the reaction processing vessel 10 by a first air channel 129. The first three-way valve 123 is arranged in the middle of the first air channel 129. The discharge port 121a of the pump 121 is connected to the second air communication port 26 of the reaction processing vessel 10 by a second air channel 130. The second three-way valve 124 is arranged in the middle of the second air channel 130.

Each of the first three-way valve 123 and the second three-way valve 124 is a three-port valve having a port A, a port B, and a port C, and can be switched between a state where the port A and the port C communicate with each other (the port B and the port C do not communicate with each other) and a state where the port B and the port C communicate with each other (the port A and the port C do not communicate with each other) under the control of the CPU 105. As the first three-way valve 123 and the second three-way valve 124, for example, a 3-port solenoid valve (LVM095R-6A) manufactured by SMC Corporation or the like can be used.

The port A of the first three-way valve 123 is connected to the discharge port 121a of the pump 121 by a first tube 125. The port C of the first three-way valve 123 is connected to the first air communication port 24 of the reaction processing vessel 10 by a second tube 126. The first tube 125 and the second tube 126 constitute the first air channel 129. A packing material 134 or a seal for securing airtightness is preferably arranged at the junction of one end of the second tube 126 and the first air communication port 24. The port B of the first three-way valve 123 is opened to the atmospheric pressure.

The first three-way valve 123 arranged as described can be switched between a state in which the first air communication port 24 of the reaction processing vessel 10 communicates with the discharge port 121a of the pump 121 and a state in which the first air communication port 24 of the reaction processing vessel 10 is opened to the atmospheric pressure. When the first air communication port 24 of the reaction processing vessel 10 communicates with the discharge port 121a of the pump 121, the first three-way valve 123 is controlled such that the port A and the port C communicate with each other. On the other hand, when the first air communication port 24 of the reaction processing vessel 10 is opened, the first three-way valve 123 is controlled such that the port B and the port C communicate with each other.

The port A of the second three-way valve 124 is connected to the discharge port 121a of the pump 121 by a third tube 127. The port C of the second three-way valve 124 is connected to the second air communication port 26 of the reaction processing vessel 10 by a fourth tube 128. The third tube 127 and the fourth tube 128 constitute the second air channel 130. A packing material 136 or a seal for securing airtightness is preferably arranged at the junction of one end of the fourth tube 128 and the second air communication port 26. The port B of the second three-way valve 124 is opened to the atmospheric pressure.

The second three-way valve 124 arranged as described can be switched between a state in which the second air communication port 26 of the reaction processing vessel 10 communicates with the discharge port 121a of the pump 121 and a state in which the second air communication port 26 of the reaction processing vessel 10 is opened to the atmospheric pressure. When the second air communication port 26 of the reaction processing vessel 10 communicates with the discharge port 121a of the pump 121, the second three-way valve 124 is controlled such that the port A and the port C communicate with each other. On the other hand, when the second air communication port 26 of the reaction processing vessel 10 is opened to the atmospheric pressure, the second three-way valve 124 is controlled such that the port B and the port C communicate with each other.

In the reaction processing apparatus 100 according to the present embodiment, by controlling the operation of the pump driver 122, the operation of the first three-way valve 123, and the operation of the second three-way valve 124, the sample 50 is moved in a reciprocating manner inside the channel such that the sample can be repeatedly exposed to each temperature region of the channel 12 of the reaction processing vessel 10, and as a result, a thermal cycle can be applied to the sample 50. More specifically, target DNA in the sample 50 is selectively amplified by repeatedly applying a step of denaturation in the high temperature region 36 and a step of annealing and elongation in the low temperature region 38. In other words, the high temperature region 36 can be considered to be a denaturation temperature region, and the low temperature region 38 can be considered to be an annealing and elongation temperature region. The time for staying in each temperature region can be appropriately set by changing the time during which the sample 50 stops at a predetermined position in each temperature region.

In the reaction processing apparatus 100 according to the present embodiment, since only one pump is used in the liquid feeding system 120, unlike the case where two pumps are used, it is not necessary to consider individual differences in pump characteristics in pump control. Since a three-way valve is based on whether the communication between a port A and a port C or the communication between a port B and a port C is established, there is no individual difference as long as a three-way valve with sufficiently small pressure loss is selected. Therefore, the control of the movement of a sample is easier in the reaction processing apparatus 100 according to the present embodiment compared to a case where two pumps are used. Further, since three-way valves are generally less expensive than pumps, the cost of the reaction processing apparatus 100 can be reduced.

FIG. 6 is a diagram for explaining a method of controlling the pump 121, the first three-way valve 123, and the second three-way valve 124 in the reaction processing apparatus 100 shown in FIG. 5. The control method explained in FIG. 6 uses, as the pump 121, a pump that allows the pressure on a primary side and the pressure on a secondary to be equal to each other when stopped.

In FIG. 6 and the subsequent FIGS., the operating state of the pump 121 (i.e., the state of discharging air) is indicated by "ON", and the non-operating state of the pump 121 (i.e., the state of stopping the discharging of air) is indicated by "OFF". Regarding the first three-way valve 123 and the second three-way valve 124, the state where the port A and the port C communicate with each other is indicated by "A-C", and the state where the port B and the port C communicate with each other is indicated by "B-C".

Step 1 shows a control state of the pump 121, the first three-way valve 123, and the second three-way valve 124 before moving the sample 50 from the low temperature region 38 to the high temperature region 36. In the step 1, the pump 121 is controlled to be in a non-operating state (OFF). Further, the first three-way valve 123 is controlled such that the port A and the port C communicate with each other (A-C), and the second three-way valve 124 is controlled such that the port B and the port C communicate with each other (B-C).

Step 2 shows a control state of the pump 121, the first three-way valve 123, and the second three-way valve 124 when moving the sample 50 from the low temperature region 38 to the high temperature region 36. In the step 2, the pump 121 is controlled to be in an operating state (ON). Further, the first three-way valve 123 is controlled such that the port A and the port C communicate with each other (A-C), and the second three-way valve 124 is controlled such that the port B and the port C communicate with each other (B-C). Thereby, the first air communication port 24 of the reaction processing vessel 10 communicates with the discharge port 121a of the pump 121, and the second air communication port 26 of the reaction processing vessel 10 is opened to the atmospheric pressure. Thus, the first air communication port 24 is under positive pressure due to the discharge of the air from the pump 121, and the sample 50 moves from the low temperature region 38 to the high temperature region 36.

Step 3 shows the control state of the pump 121, the first three-way valve 123, and the second three-way valve 124 when the sample 50 reaches the high temperature region 36. In the step 3, the pump 121 is controlled to be in a non-operating state (OFF). Further, the first three-way valve 123 is controlled such that the port A and the port C communicate with each other (A-C), and the second three-way valve 124 is controlled such that the port B and the port C communicate with each other (B-C). Thereby, both the first air communication port 24 and the second air communication port 26 are opened to the atmospheric pressure, and the sample 50 thus stops in the high temperature region 36.

Step 4 shows the control state of the pump 121, the first three-way valve 123, and the second three-way valve 124 when the sample 50 is on standby in the high temperature region 36. In the step 4, the pump 121 is controlled to be in a non-operating state (OFF). Further, the first three-way valve 123 and the second three-way valve 124 are controlled to be in either a state where the port A communicates with the port C (A-C) or a state where the port B communicates with the port C (B-C). Also at this time, since both the first air communication port 24 and the second air communication port 26 are opened to the atmospheric pressure, the sample 50 remains stopped in the high temperature region 36.

Step 5 shows a control state of the pump 121, the first three-way valve 123, and the second three-way valve 124 before moving the sample 50 from the high temperature region 36 to the low temperature region 38. In the step 5, the pump 121 is controlled to be in a non-operating state (OFF). Further, the first three-way valve 123 is controlled such that the port B and the port C communicate with each other (B-C), and the second three-way valve 124 is controlled such that the port A and the port C communicate with each other (A-C).

Step 6 shows a control state of the pump 121, the first three-way valve 123, and the second three-way valve 124 when moving the sample 50 from the high temperature region 36 to the low temperature region 38. In the step 6, the pump 121 is controlled to be in an operating state (ON). Further, the first three-way valve 123 is controlled such that the port B and the port C communicate with each other (B-C), and the second three-way valve 124 is controlled such that the port A and the port C communicate with each other (A-C). Thereby, the first air communication port 24 of the reaction processing vessel 10 is opened to the atmospheric pressure, and the second air communication port 26 of the reaction processing vessel 10 communicates with the discharge port 121a of the pump 121. Thus, the second air communication port 26 is under positive pressure due to the discharge of the air from the pump 121, and the sample 50 moves from the high temperature region 36 to the low temperature region 38.

Step 7 shows the control state of the pump 121, the first three-way valve 123, and the second three-way valve 124 when the sample 50 reaches the low temperature region 38. In the step 7, the pump 121 is controlled to be in a non-operating state (OFF). Further, the first three-way valve 123 is controlled such that the port B and the port C communicate with each other (B-C), and the second three-way valve 124 is controlled such that the port A and the port C communicate with each other (A-C). Thereby, both the first air communication port 24 and the second air communication port 26 are opened to the atmospheric pressure, and the sample 50 thus stops in the low temperature region 38.

Step 8 shows the control state of the pump 121, the first three-way valve 123, and the second three-way valve 124 when the sample 50 is on standby in the low temperature region 38. In the step 8, the pump 121 is controlled to be in a non-operating state (OFF). Further, the first three-way valve 123 and the second three-way valve 124 are controlled to be in either a state where the port A communicates with the port C (A-C) or a state where the port B communicates with the port C (B-C). Also at this time, since both the first air communication port 24 and the second air communication port 26 are opened to the atmospheric pressure, the sample 50 remains stopped in the low temperature region 38.

By repeating the steps 1 to 8 described above, a thermal cycle can be applied to the sample 50 by continuously moving the sample 50 reciprocally between the low temperature region 38 and the high temperature region 36.

FIG. 7 is a diagram for explaining another method of controlling the pump 121, the first three-way valve 123, and the second three-way valve 124 in the reaction processing apparatus shown in FIG. 5. The control method explained in FIG. 7 uses, as the pump 121, a pump that allows the pressure on a primary side and the pressure on a secondary to be equal to each other when stopped.

Step 1 shows a control state of the pump 121, the first three-way valve 123, and the second three-way valve 124 before moving the sample 50 from the low temperature region 38 to the high temperature region 36. In the step 1, the pump 121 is controlled to be in an operating state (ON). Further, the first three-way valve 123 is controlled such that the port B and the port C communicate with each other (B-C), and the second three-way valve 124 is controlled such that the port B and the port C communicate with each other (B-C).

Step 2 shows a control state of the pump 121, the first three-way valve 123, and the second three-way valve 124 when moving the sample 50 from the low temperature region 38 to the high temperature region 36. In the step 2, the pump 121 is controlled to be in an operating state (ON). Further, the first three-way valve 123 is controlled such that the port A and the port C communicate with each other (A-C), and the second three-way valve 124 is controlled such that the port B and the port C communicate with each other (B-C). Thereby, the first air communication port 24 of the reaction processing vessel 10 communicates with the discharge port 121a of the pump 121, and the second air communication port 26 of the reaction processing vessel 10 is opened to the atmospheric pressure. Thus, the first air communication port 24 is under positive pressure due to the discharge of the air from the pump 121, and the sample 50 moves from the low temperature region 38 to the high temperature region 36.

Step 3 shows the control state of the pump 121, the first three-way valve 123, and the second three-way valve 124 when the sample 50 reaches the high temperature region 36. In the step 3, the pump 121 is controlled to be in an operating state (ON). Further, the first three-way valve 123 is controlled such that the port B and the port C communicate with each other (B-C), and the second three-way valve 124 is controlled such that the port B and the port C communicate with each other (B-C). Thereby, both the first air communication port 24 and the second air communication port 26 are opened to the atmospheric pressure, and the sample 50 thus stops in the high temperature region 36.

Step 4 shows the control state of the pump 121, the first three-way valve 123, and the second three-way valve 124 when the sample 50 is on standby in the high temperature region 36. In the step 4, the pump 121 is controlled to be in a non-operating state (OFF). Further, the first three-way valve 123 and the second three-way valve 124 are controlled to be in either a state where the port A communicates with the port C (A-C) or a state where the port B communicates with the port C (B-C). Also at this time, since both the first air communication port 24 and the second air communication port 26 are opened to the atmospheric pressure, the sample 50 remains stopped in the high temperature region 36.

Step 5 shows a control state of the pump 121, the first three-way valve 123, and the second three-way valve 124 before moving the sample 50 from the high temperature region 36 to the low temperature region 38. In the step 5, the pump 121 is controlled to be in an operating state (ON). Further, the first three-way valve 123 is controlled such that the port B and the port C communicate with each other (B-C), and the second three-way valve 124 is controlled such that the port B and the port C communicate with each other (B-C).

Step 6 shows a control state of the pump 121, the first three-way valve 123, and the second three-way valve 124 when moving the sample 50 from the high temperature region 36 to the low temperature region 38. In the step 6, the pump 121 is controlled to be in an operating state (ON). Further, the first three-way valve 123 is controlled such that the port B and the port C communicate with each other (B-C), and the second three-way valve 124 is controlled such that the port A and the port C communicate with each other (A-C). Thereby, the first air communication port 24 of the reaction processing vessel 10 is opened to the atmospheric pressure, and the second air communication port 26 of the reaction processing vessel 10 communicates with the discharge port 121a of the pump 121. Thus, the second air communication port 26 is under positive pressure due to the discharge of the air from the pump 121, and the sample 50 moves from the high temperature region 36 to the low temperature region 38.

Step 7 shows the control state of the pump 121, the first three-way valve 123, and the second three-way valve 124 when the sample 50 reaches the low temperature region 38. In the step 7, the pump 121 is controlled to be in an operating state (ON). Further, the first three-way valve 123 is controlled such that the port B and the port C communicate with each other (B-C), and the second three-way valve 124 is controlled such that the port B and the port C communicate with each other (B-C). Thereby, both the first air communication port 24 and the second air communication port 26 are opened to the atmospheric pressure, and the sample 50 thus stops in the low temperature region 38.

Step 8 shows the control state of the pump 121, the first three-way valve 123, and the second three-way valve 124 when the sample 50 is on standby in the low temperature region 38. In the step 8, the pump 121 is controlled to be in a non-operating state (OFF). Further, the first three-way valve 123 and the second three-way valve 124 are controlled to be in either a state where the port A communicates with the port C (A-C) or a state where the port B communicates with the port C (B-C). Also at this time, since both the first air communication port 24 and the second air communication port 26 are opened to the atmospheric pressure, the sample 50 remains stopped in the low temperature region 38.

By repeating the steps 1 to 8 described above, a thermal cycle can be applied to the sample 50 by continuously moving the sample 50 reciprocally between the low temperature region 38 and the high temperature region 36.

In order to confirm the effect of the reaction processing apparatus 100 formed as described above, an experiment was performed where a specific bacterial strain was amplified by PCR using the reaction processing apparatus 100 according to the present embodiment. The control method described in FIG. 6 above was used here. In an attempt to detect Vero toxin VT1, PCR reagents were prepared using a KAPA3G Plant PCR kit, which is a PCR enzyme from NIPPON Genetics Co., Ltd., in the manner shown in the table below.

TABLE 1

| | Final Concentration | Remarks |
|---|---|---|
| enzyme | 0.1 U/µL | KAPA 3G Plant (NIPPON Genetics Co., Ltd.) |
| Primer F | 720 nM | 5'-GGA TAA TTT GTT TGC AGT TGA TGTC-3' (manufactured by NIHON GENE RESEARCH LABORATORIES Inc.) |
| Primer R | 720 nM | 5'-CAA ATC CTG TCA CAT ATA AAT TAT TTC GT-3' (manufactured by NIHON GENE RESEARCH LABORATORIES Inc.) |
| probe | 240 nM | 5'-CCG TAG ATT ATT AAA CCG CCC TTC CTC TGG A-3' FAM is used for fluorescent dye and quencher is of a dark type (manufactured by NIHON GENE RESEARCH LABORATORIES Inc.) |
| Additional Mg | 1.25 mM | MgCl$_2$ solution attached to KAPA 3G Plant |
| Buffer + purified water | | In accordance with the KAPA 3G Plant manual, buffer and water are blended such that the concentration of the buffer attached to the kit is lowered down to ½ with respect to the total reagent. |

On the other hand, a 20,000 copies/µL template was prepared and diluted to prepare aqueous solutions having template concentrations of 20,000, 1,000, 100, and 10 copies/µL.

Furthermore, 1 µL of an aqueous solution containing a template of each concentration was added to 19 µL of the KAPA 3G Plant solution prepared above so as to obtain 20 µL of a positive (positive control) reagent.

For a sample of the above concentration, in the reaction processing apparatus 100, the temperature of the high temperature region 36 was set to 96° C., the temperature of the low temperature region 38 was set to 62° C., the standby time in the high temperature region 36 was 3.5 seconds, the standby time in the low temperature region 38 was 15 seconds, and 50 thermal cycles (50 Ct) were then performed so as to carry out PCR. The liquid feeding time was about one second. The standby time in the high temperature region 36 in the first cycle was 15 seconds.

Figure 8:
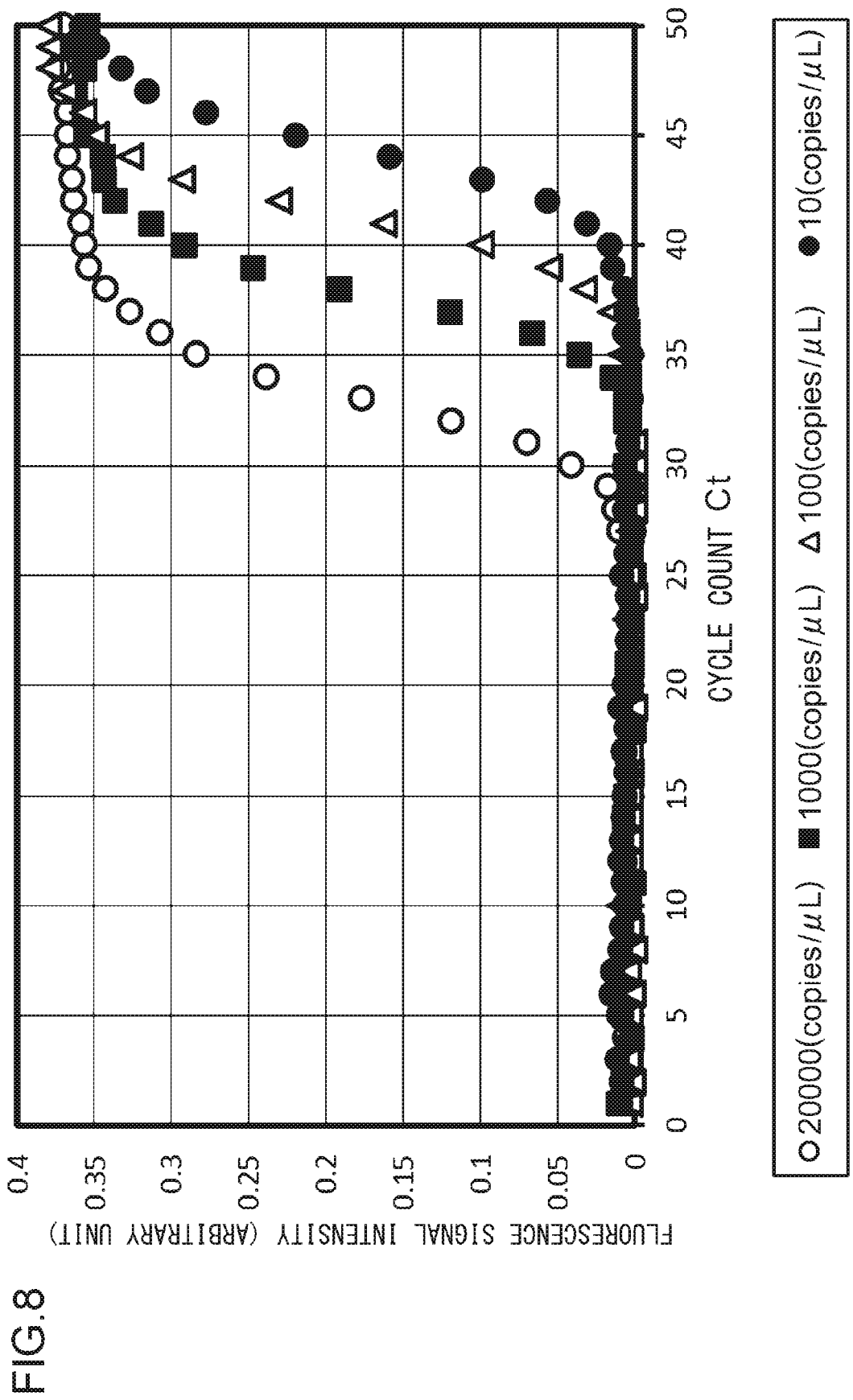
FIG. 8 is a diagram showing a PCR amplification result by the reaction processing apparatus according to the present embodiment.

FIG. 8 shows a PCR amplification result by the reaction processing apparatus 100 according to the present embodiment. In FIG. 8, the horizontal axis represents the cycle count (Ct), and the vertical axis represents the fluorescence signal intensity (arbitrary unit). Using the reaction processing apparatus 100 described above, the intensity of a fluorescence signal detected by the fluorescence detector 140 with respect to the number of cycles was measured. As a specimen in the sample was amplified, the fluorescence signal intensity increased.

Here, PCR was performed on samples containing specimens having initial concentrations of 20,000 copies/μL, 1,000 copies/μL, 100 copies/μL, and 10 copies μL, respectively. As shown in FIG. 8, the fluorescence signal intensity of the sample of 20,000 copies/μL sharply rises from around 30 cycles. Further, the fluorescence signal intensity of the sample of 1,000 copies/μL sharply rises from around 35 cycles. Further, the fluorescence signal intensity of the sample of 100 copies/μL sharply rises from around 38 cycles. Also, the fluorescence signal intensity of the sample of 10 copies/μL sharply rises from around 41 cycles. Such a sharp rise of the fluorescence signal intensity indicates the amplification of a specimen in the sample, and it can be found that good PCR can be performed using the reaction processing apparatus 100 according to the present embodiment.

Figure 9:
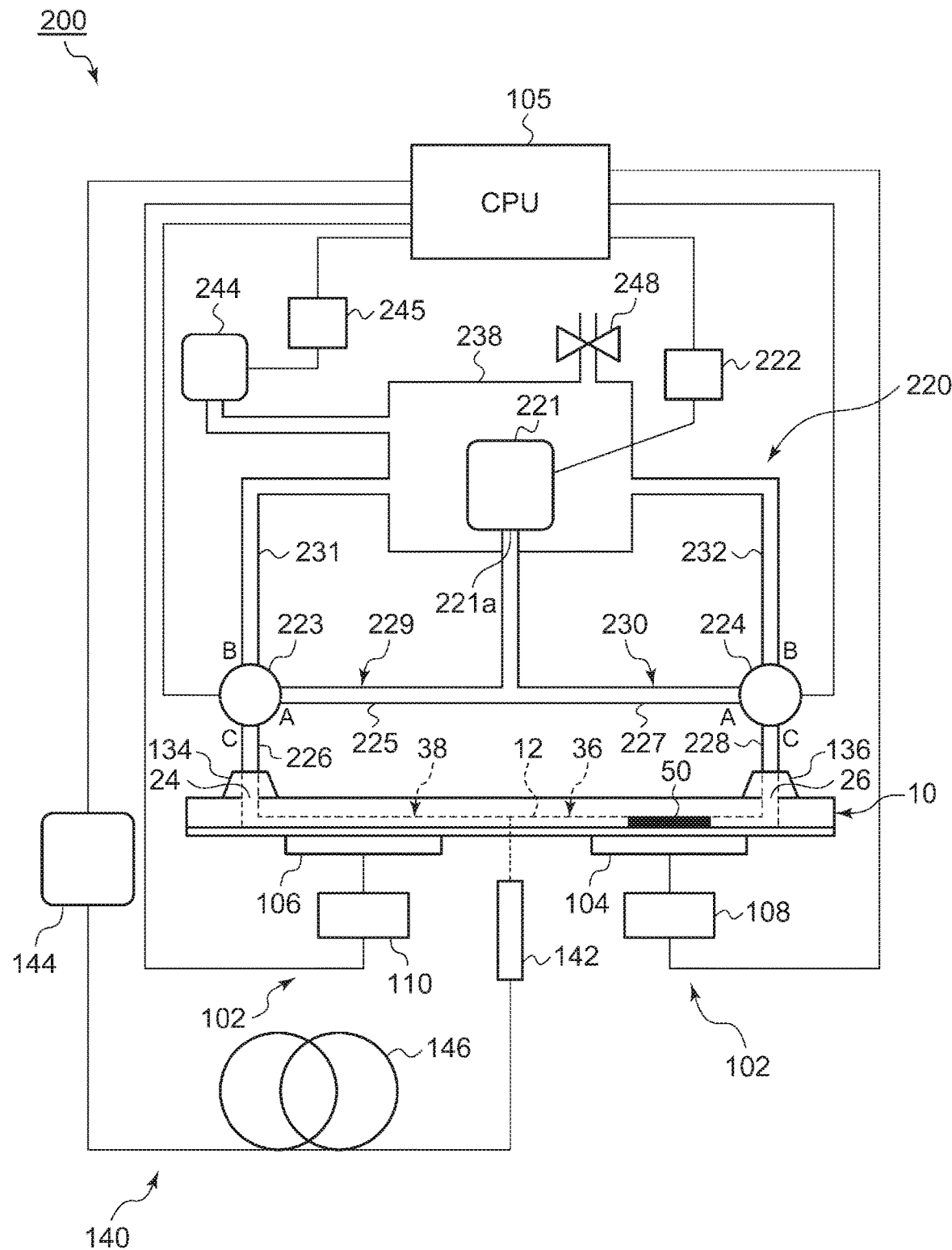
FIG. 9 is a schematic diagram for explaining a reaction processing apparatus according to another embodiment of the present invention.

FIG. 9 is a schematic diagram for explaining a reaction processing apparatus 200 according to another embodiment of the present invention. In PCR, the high temperature region is usually set to about 95° C. Since the sample is an aqueous solution, the boiling point decreases at high altitudes. For example, the pressure is roughly 897 hPa and the boiling point is 96.6° C. according to calculations at a place where the altitude is 1000 m, the pressure is 845 hPa and the boiling point is 95° C. at a place where the altitude is 1500 m, and the pressure is 797 hPa and the boiling point is 93.4° C. at a place where the altitude is 2000 m. In such places, it is sometimes difficult to perform PCR because the sample is easily boiled and vaporized and/or foamed in a high temperature region, or the sample is significantly evaporated. The reaction processing apparatus 200 according to the present embodiment can perform PCR even in such a place having a low atmospheric pressure while preventing boiling of a sample and generation of bubbles.

In the reaction processing apparatus 200, the configuration of a liquid feeding system 220 is different from that of the liquid feeding system 120 of the reaction processing apparatus 100 shown in FIG. 5. Just like the liquid feeding system 120, the liquid feeding system 220 includes a pump 221, a pump driver 222 for driving the pump 221, a first three-way valve 223, and a second three-way valve 224. The pump driver 222, the first three-way valve 223, and the second three-way valve 224 are controlled by the CPU 105.

The liquid feeding system 220 according to the present embodiment further includes a pressurizing chamber 238, a pressurizing chamber pump 244, and a pressurizing chamber pump driver 245 for controlling the pressurizing chamber pump 244. In the present embodiment, a pump 221 for feeding a liquid is arranged inside the pressurizing chamber 238.

The pressurizing chamber 238 forms a space having a certain volume therein. A pressurizing chamber pump 244 is connected to the pressurizing chamber 238. The pressurizing chamber pump driver 245 controls the pressurizing chamber pump 244 such that the space inside the pressurizing chamber 238 has a predetermined pressure in accordance with an instruction from the CPU 105. As the pressurizing chamber pump 244, a rolling pump (model: RSP08D-02RW) manufactured by OKEN SEIKO co., ltd., or the like can be used, and a means of pressurization by a rubber ball, a syringe, or the like can be also used as a simple means.

In the present embodiment, the pressure inside the pressurizing chamber 238 is maintained at a value higher than the pressure in the surrounding environment of the reaction processing apparatus 200 (for example, 1.3 atm) during the reaction process. The atmospheric pressure in the surrounding environment of the reaction processing apparatus 200 means the pressure (or atmospheric pressure) at a place where the reaction processing apparatus 200 is installed, a place where the PCR is performed by the reaction processing apparatus 200, or, when the reaction processing apparatus 200 is installed at a place that is partitioned from the surroundings, the partitioned place. The pressure inside the pressurizing chamber 238 needs to be applied to such an extent that significant evaporation of the sample and generation of air bubbles or the like, which affect the reaction process involving PCR, can be prevented even when the sample is repeatedly exposed to a high temperature (about 95° C.). The higher the pressure inside the pressurizing chamber 238 becomes, the more the influence of the evaporation of the sample and the like can be suppressed. However, on the other hand, the liquid feeding system 220 becomes complicated or enlarged including the handling thereof. Thus, a person skilled in the art can comprehensively judge the application, purpose, cost, effect, etc., of the processor so as to design the entire system.

An atmospheric pressure releasing valve 248 is provided in the pressurizing chamber 238. The atmospheric pressure releasing valve 248 is controlled such that the pressure of the liquid feeding system 220 and the pressure of the reaction processing vessel 10 in the channel 12 become equal to the atmospheric pressure at the time of installing or removing the reaction processing vessel 10. Thereby, rapid movement and squirting of the sample 50 can be prevented. In addition, during the reaction process, the pressurizing chamber pump 244 is stopped and the atmospheric pressure releasing valve 248 is left open so that a reaction processing apparatus substantially equivalent to the reaction processing apparatus 100 is achieved.

Further, a pressure sensor (not shown) for constantly monitoring the pressure of the internal space thereof may be provided in the pressurizing chamber 238. By sending the actual pressure detected by the pressure sensor to the CPU 105, the pressure inside the pressurizing chamber 238 can be suitably controlled.

Also in the present embodiment, a pump of a type in which the pressure on the primary side and the pressure on the secondary side become equal at the time of stoppage can be used as the pump 221.

The discharge port 221a of the pump 221 is connected to the first air communication port 24 of the reaction processing vessel 10 by a first air channel 229. The first three-way valve 223 is arranged in the middle of the first air channel 229. The discharge port 221a of the pump 121 is connected to the second air communication port 26 of the reaction processing vessel 10 by a second air channel 230. The second three-way valve 224 is arranged in the middle of the second air channel 230.

The port A of the first three-way valve 223 is connected to the discharge port 221a of the pump 221 by a first tube 225. The port C of the first three-way valve 223 is connected to the first air communication port 24 of the reaction processing vessel 10 by a second tube 226. The first tube 225 and the second tube 226 constitute the first air channel 229. The port B of the first three-way valve 223 communicates with the internal space of the pressurizing chamber 238 by a fifth tube 231.

The first three-way valve 223 arranged as described can be switched between a state in which the first air communication port 24 of the reaction processing vessel 10 communicates with the discharge port 221a of the pump 221 and a state in which the first air communication port 24 of the reaction processing vessel 10 is open to the internal space of the pressurizing chamber 238. When the first air communication port 24 of the reaction processing vessel 10 communicates with the discharge port 221a of the pump 221, the first three-way valve 223 is controlled such that the port A and the port C communicate with each other. On the other hand, when the first air communication port 24 of the reaction processing vessel 10 is opened to the internal space of the pressurizing chamber 238, the first three-way valve 223 is controlled such that the port B and the port C communicate with each other.

The port A of the second three-way valve 224 is connected to the discharge port 221a of the pump 221 by a third tube 227. The port C of the second three-way valve 224 is connected to the second air communication port 26 of the reaction processing vessel 10 by a fourth tube 228. The third tube 227 and the fourth tube 228 constitute the second air channel 230. The port B of the second three-way valve 224 communicates with the internal space of the pressurizing chamber 238 by a sixth tube 232.

The second three-way valve 224 arranged as described can be switched between a state in which the second air communication port 26 of the reaction processing vessel 10 communicates with the discharge port 221a of the pump 221 and a state in which the second air communication port 26 of the reaction processing vessel 10 is open to the internal space of the pressurizing chamber 238. When the second air communication port 26 of the reaction processing vessel 10 communicates with the discharge port 221a of the pump 221, the second three-way valve 224 is controlled such that the port A and the port C communicate with each other. On the other hand, when the second air communication port 26 of the reaction processing vessel 10 is opened to the internal space of the pressurizing chamber 238, the second three-way valve 224 is controlled such that the port B and the port C communicate with each other.

In the reaction processing apparatus 200 according to the present embodiment, by controlling the operation of the pump driver 222, the operation of the first three-way valve 223, and the operation of the second three-way valve 224, the sample 50 is moved in a reciprocating manner inside the channel such that the sample can be repeatedly exposed to each temperature region of the channel 12 of the reaction processing vessel 10, and as a result, a thermal cycle can be applied to the sample 50. Further, the use of one pump makes it easy to control the movement of the sample and allows for the cost to be reduced, in the same way as in the above-described reaction processing apparatus 100.

Further, in the reaction processing apparatus 200 according to the present embodiment, the pump 221 is arranged in the internal space of the pressurizing chamber 238 set to a pressure higher than the pressure of the surrounding environment (for example, 1.3 atm), and the port B of the first three-way valve 223 and the port B of the second three-way valve 224 are configured to be opened to the internal space of the pressurizing chamber 238. Therefore, during the reaction process, the entire channel 12 is maintained at a pressure higher than the atmospheric pressure of the surrounding environment. For this reason, even under a low atmospheric pressure environment such as high altitude, it is possible to prevent the boiling point of the sample 50 mainly composed of an aqueous solution from lowering and the sample 50 from boiling and/or foaming, and to stable PCR can thus be performed.

For the method of controlling the pump driver 222, the first three-way valve 223, and the second three-way valve 224 in the reaction processing apparatus 200, the method shown in FIG. 6 can be used. The control method will be described with reference to FIG. 6 again. As the pump 221, a pump that allows the pressure on the primary side and the pressure on the secondary side to become equal when stopped is used. In the reaction processing apparatus 200, the atmospheric pressure releasing valve 248 is closed, the pump 244 for the pressurizing chamber is operated, the pressure in the internal space of the pressurizing chamber 238 is increased, and the inside of each tube and the channel 12 is increased, all in advance. The first three-way valve 223 and the second three-way valve 224 at this time are controlled to be in either a state where the port A communicates with the port C (A-C) or a state where the port B communicates with the port C (B-C).

Step 1 shows a control state of the pump 221, the first three-way valve 223, and the second three-way valve 224 before moving the sample 50 from the low temperature region 38 to the high temperature region 36. In the step 1, the pump 221 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C).

Step 2 shows a control state of the pump 221, the first three-way valve 223, and the second three-way valve 224 when moving the sample 50 from the low temperature region 38 to the high temperature region 36. In the step 2, the pump 221 is controlled to be in an operating state (ON). Further, the first three-way valve 223 is controlled such that the port A and the port C communicate with each other (A-C), and the second three-way valve 224 is controlled such that the port B and the port C communicate with each other (B-C). Thereby, the first air communication port 24 of the reaction processing vessel 10 communicates with the discharge port 221a of the pump 221, and the second air communication port 26 of the reaction processing vessel 10 is opened to the internal space of the pressurizing chamber 238. In the present embodiment, since the pump 221 is arranged inside the pressurizing chamber 238, when air is discharged from the pump 221, the pressure at the first air communication port 24 of the reaction processing vessel 10 becomes higher than that at the second air communication port 26, and the sample 50 thus moves from the low temperature region 38 to the high temperature region 36.

Step 3 shows the control state of the pump 221, the first three-way valve 223, and the second three-way valve 224 when the sample 50 reaches the high temperature region 36. In the step 3, the pump 221 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C). Thereby, both the first air communication port 24 and the second air communication port 26 are opened to the internal space of the pressurizing chamber 238, and the sample 50 thus stops in the high temperature region 36.

Step 4 shows the control state of the pump 221, the first three-way valve 223, and the second three-way valve 224 when the sample 50 is on standby in the high temperature region 36. In the step 4, the pump 221 is controlled to be in a non-operating state (OFF). Further, the first three-way valve 223 and the second three-way valve 224 are controlled to be in either a state where the port A communicates with the port C (A-C) or a state where the port B communicates with the port C (B-C). Both the first air communication port 24 and the second air communication port 26 are opened to the internal space of the pressurizing chamber 238, and the sample 50 thus remains stopped in the high temperature region 36 also at this time.

Step 5 shows a control state of the pump 221, the first three-way valve 223, and the second three-way valve 224 before moving the sample 50 from the high temperature region 36 to the low temperature region 38. In the step 5, the pump 221 is controlled to be in a non-operating state (OFF). Further, the first three-way valve 223 is controlled such that the port B and the port C communicate with each other (B-C), and the second three-way valve 224 is controlled such that the port A and the port C communicate with each other (A-C).

Step 6 shows a control state of the pump 221, the first three-way valve 223, and the second three-way valve 224 when moving the sample 50 from the high temperature region 36 to the low temperature region 38. In the step 6, the pump 221 is controlled to be in an operating state (ON). Further, the first three-way valve 223 is controlled such that the port B and the port C communicate with each other (B-C), and the second three-way valve 224 is controlled such that the port A and the port C communicate with each other (A-C). Thereby, the first air communication port 24 of the reaction processing vessel 10 is opened to the internal space of the pressurizing chamber 238, and the second air communication port 26 of the reaction processing vessel 10 communicates with the discharge port 221a of the pump 221. Therefore, when air is discharged from the pump 221, the pressure at the second air communication port 26 of the reaction processing vessel 10 becomes higher than that at the first air communication port 24, and the sample 50 thus moves from the high temperature region 36 to the low temperature region 38.

Step 7 shows the control state of the pump 221, the first three-way valve 223, and the second three-way valve 224 when the sample 50 reaches the low temperature region 38. In the step 7, the pump 221 is controlled to be in a non-operating state (OFF). Further, the first three-way valve 223 is controlled such that the port B and the port C communicate with each other (B-C), and the second three-way valve 224 is controlled such that the port A and the port C communicate with each other (A-C). Thereby, both the first air communication port 24 and the second air communication port 26 are opened to the internal space of the pressurizing chamber 238, and the sample 50 thus stops in the low temperature region 38.

Step 8 shows the control state of the pump 221, the first three-way valve 223, and the second three-way valve 224 when the sample 50 is on standby in the low temperature region 38. In the step 8, the pump 221 is controlled to be in a non-operating state (OFF). Further, the first three-way valve 223 and the second three-way valve 224 are controlled to be in either a state where the port A communicates with the port C (A-C) or a state where the port B communicates with the port C (B-C). Both the first air communication port 24 and the second air communication port 26 are opened to the internal space of the pressurizing chamber 238, and the sample 50 thus remains stopped in the low temperature region 38 also at this time.

By repeating the steps 1 to 8 described above, a thermal cycle can be applied to the sample 50 by continuously moving the sample 50 reciprocally between the low temperature region 38 and the high temperature region 36.

For the method of controlling the pump driver 222, the first three-way valve 223, and the second three-way valve 224 in the reaction processing apparatus 200, the method shown in FIG. 7 can be also used. The control method will be described with reference to FIG. 7 again. This control method uses, as the pump 221, a pump that allows the pressure on a primary side and the pressure on a secondary to be equal to each other when stopped. In the same way, in the reaction processing apparatus 200, the atmospheric pressure releasing valve 248 is closed, the pump 244 for the pressurizing chamber is operated, the pressure in the internal space of the pressurizing chamber 238 is increased, and the inside of each tube and the channel 12 is increased, all in advance.

Step 1 shows a control state of the pump 221, the first three-way valve 223, and the second three-way valve 224 before moving the sample 50 from the low temperature region 38 to the high temperature region 36. In the step 1, the pump 221 is controlled to be in an operating state (ON). Further, the first three-way valve 223 is controlled such that the port B and the port C communicate with each other (B-C), and the second three-way valve 224 is controlled such that the port B and the port C communicate with each other (B-C).

Step 2 shows a control state of the pump 221, the first three-way valve 223, and the second three-way valve 224 when moving the sample 50 from the low temperature region 38 to the high temperature region 36. In the step 2, the pump 221 is controlled to be in an operating state (ON). Further, the first three-way valve 223 is controlled such that the port A and the port C communicate with each other (A-C), and the second three-way valve 224 is controlled such that the port B and the port C communicate with each other (B-C). Thereby, the first air communication port 24 of the reaction processing vessel 10 communicates with the discharge port 221a of the pump 221, and the second air communication port 26 of the reaction processing vessel 10 is opened to the internal space of the pressurizing chamber 238. In the present embodiment, since the pump 221 is arranged inside the pressurizing chamber 238, when air is discharged from the pump 221, the pressure at the first air communication port 24 of the reaction processing vessel 10 becomes higher than that at the second air communication port 26, and the sample 50 thus moves from the low temperature region 38 to the high temperature region 36.

Step 3 shows the control state of the pump 221, the first three-way valve 223, and the second three-way valve 224 when the sample 50 reaches the high temperature region 36. In the step 3, the pump 221 is controlled to be in an operating state (ON). Further, the first three-way valve 223 is controlled such that the port B and the port C communicate with each other (B-C), and the second three-way valve 224 is controlled such that the port B and the port C communicate with each other (B-C). Thereby, both the first air communication port 24 and the second air communication port 26 are opened to the internal space of the pressurizing chamber 238, and the sample 50 thus stops in the high temperature region 36.

Step 4 shows the control state of the pump 221, the first three-way valve 223, and the second three-way valve 224 when the sample 50 is on standby in the high temperature region 36. In the step 4, the pump 221 is controlled to be in a non-operating state (OFF). Further, the first three-way valve 223 and the second three-way valve 224 are controlled to be in either a state where the port A communicates with the port C (A-C) or a state where the port B communicates with the port C (B-C). Both the first air communication port 24 and the second air communication port 26 are opened to the internal space of the pressurizing chamber 238, and the sample 50 thus remains stopped in the high temperature region 36 also at this time.

Step 5 shows a control state of the pump 221, the first three-way valve 223, and the second three-way valve 224 before moving the sample 50 from the high temperature region 36 to the low temperature region 38. In the step 5, the pump 221 is controlled to be in an operating state (ON). Further, the first three-way valve 223 is controlled such that the port B and the port C communicate with each other (B-C), and the second three-way valve 224 is controlled such that the port B and the port C communicate with each other (B-C).

Step 6 shows a control state of the pump 221, the first three-way valve 223, and the second three-way valve 224 when moving the sample 50 from the high temperature region 36 to the low temperature region 38. In the step 6, the pump 221 is controlled to be in an operating state (ON). Further, the first three-way valve 223 is controlled such that the port B and the port C communicate with each other (B-C), and the second three-way valve 224 is controlled such that the port A and the port C communicate with each other (A-C). Thereby, the first air communication port 24 of the reaction processing vessel 10 is opened to the internal space of the pressurizing chamber 238, and the second air communication port 26 of the reaction processing vessel 10 communicates with the discharge port 221a of the pump 221. Therefore, when air is discharged from the pump 221, the pressure at the second air communication port 26 of the reaction processing vessel 10 becomes higher than that at the first air communication port 24, and the sample 50 thus moves from the high temperature region 36 to the low temperature region 38.

Step 7 shows the control state of the pump 221, the first three-way valve 223, and the second three-way valve 224 when the sample 50 reaches the low temperature region 38. In the step 7, the pump 221 is controlled to be in an operating state (ON). Further, the first three-way valve 223 is controlled such that the port B and the port C communicate with each other (B-C), and the second three-way valve 224 is controlled such that the port B and the port C communicate with each other (B-C). Thereby, both the first air communication port 24 and the second air communication port 26 are opened to the internal space of the pressurizing chamber 238, and the sample 50 thus stops in the low temperature region 38.

Step 8 shows the control state of the pump 221, the first three-way valve 223, and the second three-way valve 224 when the sample 50 is on standby in the low temperature region 38. In the step 8, the pump 221 is controlled to be in a non-operating state (OFF). Further, the first three-way valve 223 and the second three-way valve 224 are controlled to be in either a state where the port A communicates with the port C (A-C) or a state where the port B communicates with the port C (B-C). Both the first air communication port 24 and the second air communication port 26 are opened to the internal space of the pressurizing chamber 238, and the sample 50 thus remains stopped in the low temperature region 38 also at this time.

By repeating the steps 1 to 8 described above, a thermal cycle can be applied to the sample 50 by continuously moving the sample 50 reciprocally between the low temperature region 38 and the high temperature region 36.

Figure 10:
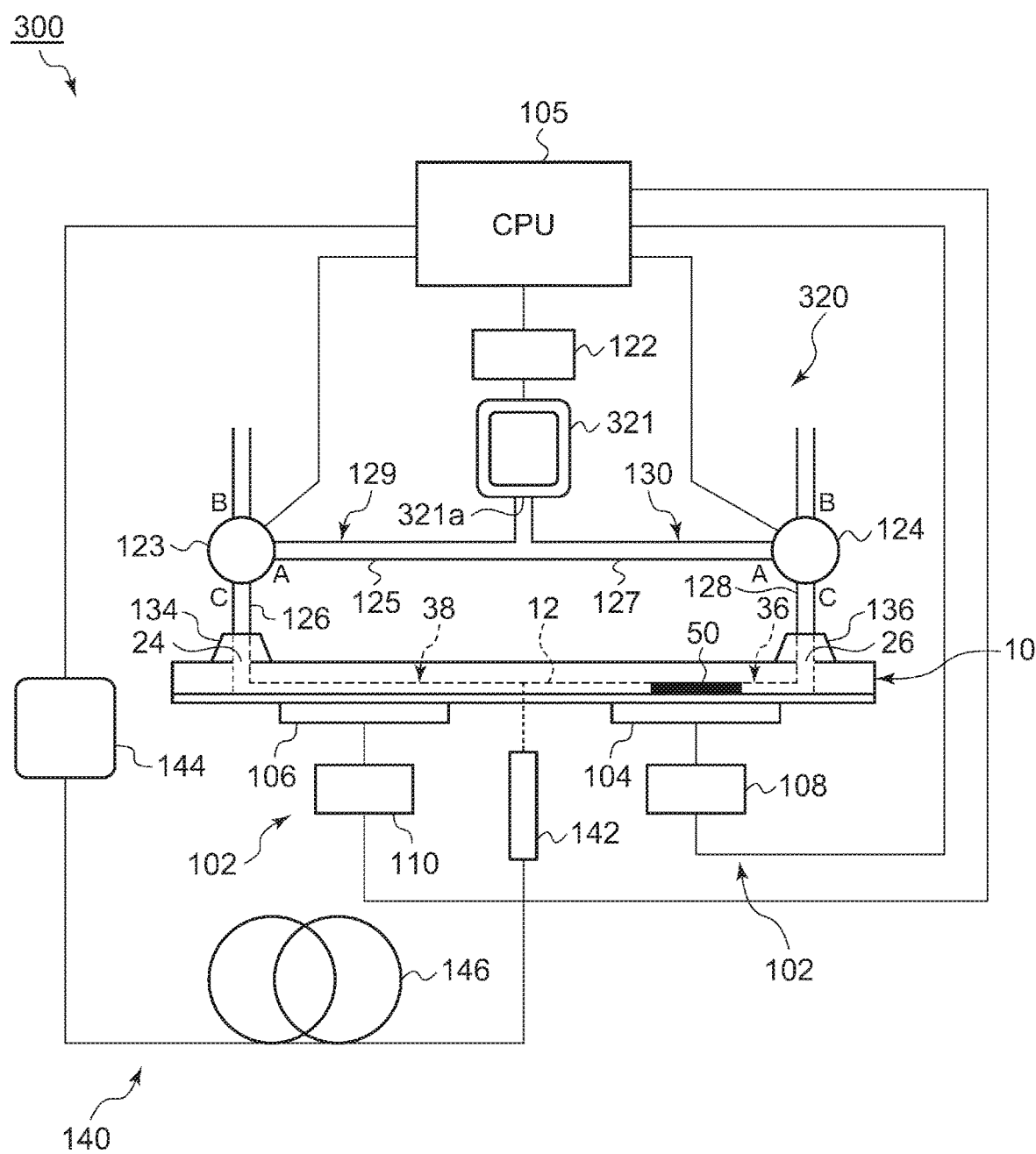
FIG. 10 is a schematic diagram for explaining a reaction processing apparatus according to yet another embodiment of the present invention.

FIG. 10 is a schematic diagram for explaining a reaction processing apparatus 300 according to yet another embodiment of the present invention. This reaction processing apparatus 300 differs from the reaction processing apparatus 100 shown in FIG. 5 in that a pump 321 is used in which the pressure on the primary side and the pressure on the secondary side do not become equal to each other when stopped in a liquid feeding system 320. As such a pump 321, for example, a piezo micro pump (model SDMP302 (306)) manufactured by Takasago Electric, Inc., can be used.

FIG. 11 is a diagram for explaining a method of controlling the pump 321, the first three-way valve 123, and the second three-way valve 124 in the reaction processing apparatus 300 shown in FIG. 10.

Step 1 shows a control state of the pump 321, the first three-way valve 123, and the second three-way valve 124 before moving the sample 50 from the low temperature region 38 to the high temperature region 36. In the step 1, the pump 321 is controlled to be in a non-operating state (OFF). Further, the first three-way valve 123 is controlled such that the port A and the port C communicate with each other (A-C), and the second three-way valve 124 is controlled such that the port B and the port C communicate with each other (B-C).

Step 2 shows a control state of the pump 321, the first three-way valve 123, and the second three-way valve 124 when moving the sample 50 from the low temperature region 38 to the high temperature region 36. In the step 2, the pump 321 is controlled to be in an operating state (ON). Further, the first three-way valve 123 is controlled such that the port A and the port C communicate with each other (A-C), and the second three-way valve 124 is controlled such that the port B and the port C communicate with each other (B-C).

Step 3 shows the control state of the pump 321, the first three-way valve 123, and the second three-way valve 124 when the sample 50 reaches the high temperature region 36. In the step 3, the pump 321 is controlled to be in a non-operating state (OFF). Further, the first three-way valve 123 is controlled such that the port A and the port C communicate with each other (A-C), and the second three-way valve 124 is controlled such that the port B and the port C communicate with each other (B-C).

Step 4 shows the control state of the pump 321, the first three-way valve 123, and the second three-way valve 124 when the sample 50 is on standby in the high temperature region 36. In the step 4, the pump 321 is controlled to be in a non-operating state (OFF). Further, the first three-way valve 123 and the second three-way valve 124 are controlled to be both in a state where the port A communicates with the port C (A-C) or a state where the port B communicates with the port C (B-C).

Step 5 shows a control state of the pump 321, the first three-way valve 123, and the second three-way valve 124 before moving the sample 50 from the high temperature region 36 to the low temperature region 38. In the step 5, the pump 321 is controlled to be in a non-operating state (OFF). Further, the first three-way valve 123 is controlled such that the port B and the port C communicate with each other (B-C), and the second three-way valve 124 is controlled such that the port A and the port C communicate with each other (A-C).

Step 6 shows a control state of the pump 321, the first three-way valve 123, and the second three-way valve 124 when moving the sample 50 from the high temperature region 36 to the low temperature region 38. In the step 6, the pump 321 is controlled to be in an operating state (ON). Further, the first three-way valve 123 is controlled such that the port B and the port C communicate with each other (B-C), and the second three-way valve 124 is controlled such that the port A and the port C communicate with each other (A-C).

Step 7 shows the control state of the pump 321, the first three-way valve 123, and the second three-way valve 124 when the sample 50 reaches the low temperature region 38. In the step 7, the pump 321 is controlled to be in a non-operating state (OFF). Further, the first three-way valve 123 is controlled such that the port B and the port C communicate with each other (B-C), and the second three-way valve 124 is controlled such that the port A and the port C communicate with each other (A-C).

Step 8 shows the control state of the pump 321, the first three-way valve 123, and the second three-way valve 124 when the sample 50 is on standby in the low temperature region 38. In the step 8, the pump 321 is controlled to be in a non-operating state (OFF). Further, the first three-way valve 123 and the second three-way valve 124 are controlled to be both in a state where the port A communicates with the port C (A-C) or a state where the port B communicates with the port C (B-C).

By repeating the steps 1 to 8 described above, a thermal cycle can be applied to the sample 50 by continuously moving the sample 50 reciprocally between the low temperature region 38 and the high temperature region 36. Also in the reaction processing apparatus 300 according to the present embodiment, since only one pump is used, the control of the movement of the sample can be easily performed, and the cost can be reduced.

Figure 12:
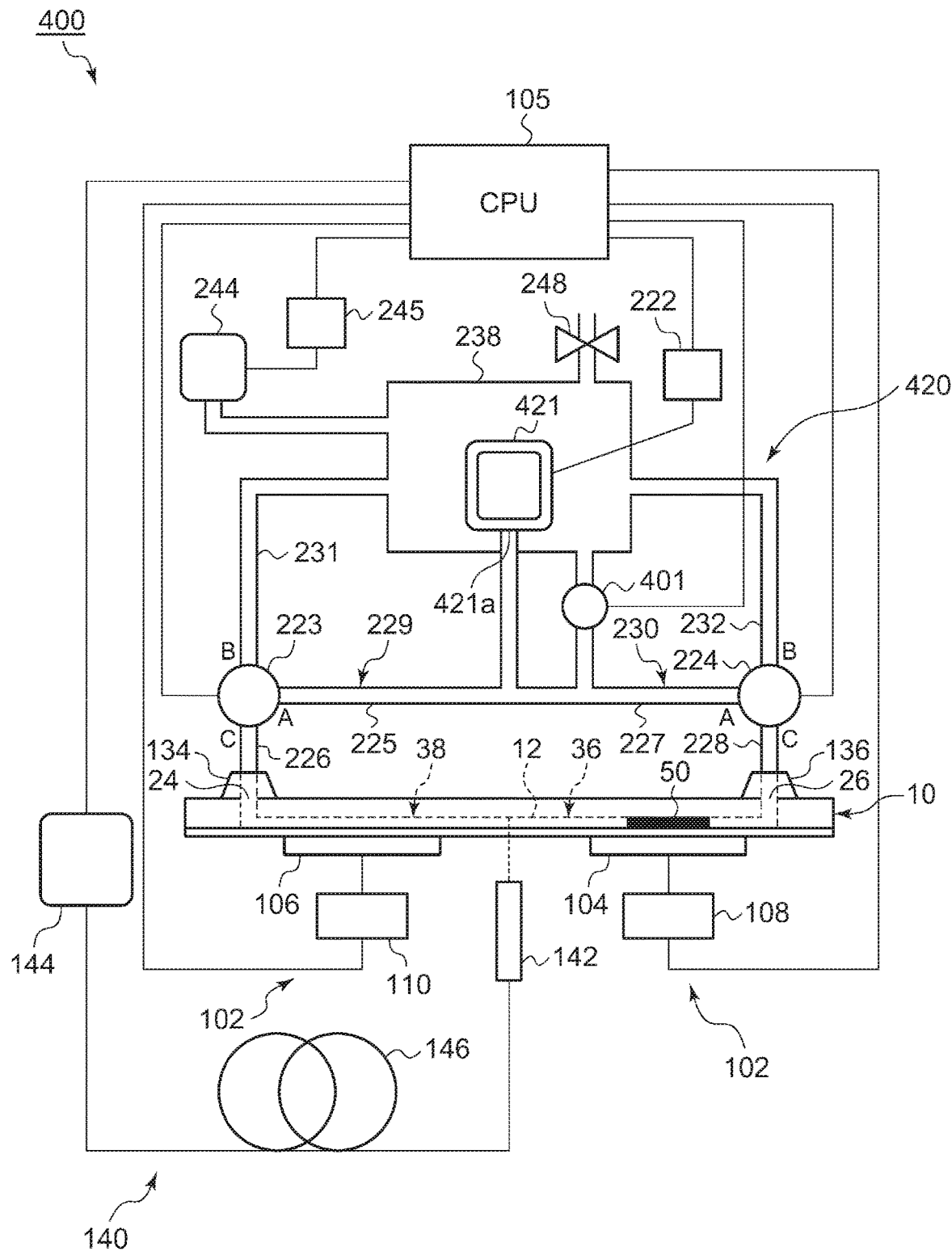
FIG. 12 is a schematic diagram for explaining a reaction processing apparatus according to yet another embodiment of the present invention.

FIG. 12 is a schematic diagram for explaining a reaction processing apparatus 400 according to yet another embodiment of the present invention. This reaction processing apparatus 400 differs from the reaction processing apparatus 200 shown in FIG. 9 in that a pump 421 is used in which the pressure on the primary side and the pressure on the secondary side do not become equal to each other when stopped in a liquid feeding system 420. As the pump 421, for example, a piezo micro pump (model SDMP302 (306)) manufactured by Takasago Electric, Inc., can be used.

The reaction processing apparatus 400 according to the present embodiment further includes a solenoid valve 401. This solenoid valve 401 is provided in a channel that connects the pressurizing chamber 238 to the first air channel 229 and the second air channel 230 and can be switched between an open state and a closed state according to an instruction from the CPU 105. When the solenoid valve 401 is in the open state, the first air channel 229 and the second air channel 230 communicate with the internal space of the pressurizing chamber 238. On the other hand, when the solenoid valve 401 is in the closed state, the first air channel 229 and the second air channel 230 do not communicate with the internal space of the pressurizing chamber 238. As the solenoid valve 401, for example, a solenoid valve (model TDS-V05B) manufactured by TDS Co., Ltd., or the like can be used.

FIG. 13 is a diagram for explaining a method of controlling the pump 421, the first three-way valve 223, the second three-way valve 224, and the solenoid valve 401 in the reaction processing apparatus 400 shown in FIG. 12.

Step 1 shows the control state of the pump 421, the first three-way valve 223, the second three-way valve 224, and the solenoid valve 401 when increasing the pressure in the internal space of the pressurizing chamber 238 and pressurizing the inside of each tube and the inside of the channel 12. In the step 1, the pump 421 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in an open state.

Step 2 shows a control state of the pump 421, the first three-way valve 223, the second three-way valve 224, and the solenoid valve 401 before moving the sample 50 from the low temperature region 38 to the high temperature region 36. In the step 2, the pump 421 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in a closed state.

Step 3 shows a control state of the pump 421, the first three-way valve 223, the second three-way valve 224, and the solenoid valve 401 when moving the sample 50 from the low temperature region 38 to the high temperature region 36. In the step 3, the pump 421 is controlled to be in an operating state (ON). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in a closed state.

Step 4 shows the control state of the pump 421, the first three-way valve 223, the second three-way valve 224, and the solenoid valve 401 when the sample 50 reaches the high temperature region 36. In the step 4, the pump 421 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in a closed state.

Step 5 shows the control state of the pump 421, the first three-way valve 223, the second three-way valve 224, and the solenoid valve 401 when the sample 50 is on standby in the high temperature region 36. In the step 5, the pump 421 is controlled to be in a non-operating state (OFF). Further, the first three-way valve 223 and the second three-way valve 224 are controlled to be both in a state where the port A communicates with the port C (A-C) or a state where the port B communicates with the port C (B-C). Further, the solenoid valve 401 is controlled to be in an open state.

Step 6 shows a control state of the pump 421, the first three-way valve 223, the second three-way valve 224, and the solenoid valve 401 before moving the sample 50 from the high temperature region 36 to the low temperature region 38. In the step 6, the pump 421 is controlled to be in a non-operating state (OFF). Further, the first three-way valve 223 is controlled such that the port B and the port C communicate with each other (B-C), and the second three-way valve 224 is controlled such that the port A and the port C communicate with each other (A-C). Further, the solenoid valve 401 is controlled to be in a closed state.

Step 7 shows a control state of the pump 421, the first three-way valve 223, the second three-way valve 224, and the solenoid valve 401 when moving the sample 50 from the high temperature region 36 to the low temperature region 38. In the step 7, the pump 421 is controlled to be in an operating state (ON). Further, the first three-way valve 223 is controlled such that the port B and the port C communicate with each other (B-C), and the second three-way valve 224 is controlled such that the port A and the port C communicate with each other (A-C). Further, the solenoid valve 401 is controlled to be in a closed state.

Step 8 shows the control state of the pump 421, the first three-way valve 223, the second three-way valve 224, and the solenoid valve 401 when the sample 50 reaches the low temperature region 38. In the step 8, the pump 421 is controlled to be in a non-operating state (OFF). Further, the first three-way valve 223 is controlled such that the port B and the port C communicate with each other (B-C), and the second three-way valve 224 is controlled such that the port A and the port C communicate with each other (A-C). Further, the solenoid valve 401 is controlled to be in a closed state.

Step 9 shows the control state of the pump 421, the first three-way valve 223, the second three-way valve 224, and the solenoid valve 401 when the sample 50 is on standby in the low temperature region 38. In the step 9, the pump 421 is controlled to be in a non-operating state (OFF). Further, the first three-way valve 223 and the second three-way valve 224 are controlled to be both in a state where the port A communicates with the port C (A-C) or a state where the port B communicates with the port C (B-C). Further, the solenoid valve 401 is controlled to be in an open state.

By repeating the steps 2 to 9 described above, a thermal cycle can be applied to the sample 50 by continuously moving the sample 50 reciprocally between the low temperature region 38 and the high temperature region 36.

For the method of controlling the pump 421, the first three-way valve 223, the second three-way valve 224, and the solenoid valve 401 in the reaction processing apparatus 400, the method shown in FIG. 14 can be also used.

Step 1 shows the control state of the pump 421, the first three-way valve 223, the second three-way valve 224, and the solenoid valve 401 when increasing the pressure in the internal space of the pressurizing chamber 238 and pressurizing the inside of each tube and the inside of the channel 12. In the step 1, the pump 421 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in an open state.

Step 2 shows a control state of the pump 421, the first three-way valve 223, the second three-way valve 224, and the solenoid valve 401 before moving the sample 50 from the low temperature region 38 to the high temperature region 36. In the step 2, the pump 421 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in a closed state.

Step 3 shows the control state of the pump 421, the first three-way valve 223, the second three-way valve 224, and the solenoid valve 401 when moving the sample 50 from the low temperature region 38 to the high temperature region 36. In the step 3, the pump 421 is controlled to be in an operating state (ON). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in a closed state.

Step 4 shows the control state of the pump 421, the first three-way valve 223, the second three-way valve 224, and the solenoid valve 401 when the sample 50 reaches the high temperature region 36. In the step 4, the pump 421 is controlled to be in a non-operating state (OFF). Further, the first three-way valve 223 is controlled such that the port A and the port C communicate with each other (A-C), and the second three-way valve 224 is controlled such that the port B and the port C communicate with each other (B-C). Further, the solenoid valve 401 is controlled to be in a closed state.

Step 5 shows the control state of the pump 421, the first three-way valve 223, the second three-way valve 224, and the solenoid valve 401 when the sample 50 is on standby in the high temperature region 36. In the step 5, the pump 221 is controlled to be in a non-operating state (OFF). Further, the first three-way valve 223 and the second three-way valve 224 are controlled to be both in a state where the port A communicates with the port C (A-C) or a state where the port B communicates with the port C (B-C). Further, the solenoid valve 401 is controlled to be in a closed state.

Step 6 shows the control state of the pump 421, the first three-way valve 223, the second three-way valve 224, and the solenoid valve 401 before moving the sample 50 from the high temperature region 36 to the low temperature region 38. In the step 6, the pump 421 is controlled to be in a non-operating state (OFF). Further, the first three-way valve 223 is controlled such that the port B and the port C communicate with each other (B-C), and the second three-way valve 224 is controlled such that the port A and the port C communicate with each other (A-C). Further, the solenoid valve 401 is controlled to be in a closed state.

Step 7 shows the control state of the pump 421, the first three-way valve 223, the second three-way valve 224, and the solenoid valve 401 when moving the sample 50 from the high temperature region 36 to the low temperature region 38. In the step 7, the pump 421 is controlled to be in an operating state (ON). Further, the first three-way valve 223 is controlled such that the port B and the port C communicate with each other (B-C), and the second three-way valve 224 is controlled such that the port A and the port C communicate with each other (A-C). Further, the solenoid valve 401 is controlled to be in a closed state.

Step 8 shows the control state of the pump 421, the first three-way valve 223, the second three-way valve 224, and the solenoid valve 401 when the sample 50 reaches the low temperature region 38. In the step 8, the pump 421 is controlled to be in a non-operating state (OFF). Further, the first three-way valve 223 is controlled such that the port B and the port C communicate with each other (B-C), and the second three-way valve 224 is controlled such that the port A and the port C communicate with each other (A-C). Further, the solenoid valve 401 is controlled to be in a closed state.

Step 9 shows the control state of the pump 421, the first three-way valve 223, the second three-way valve 224, and the solenoid valve 401 when the sample 50 is on standby in the low temperature region 38. In the step 9, the pump 421 is controlled to be in a non-operating state (OFF). Further, the first three-way valve 223 and the second three-way valve 224 are controlled to be both in a state where the port A communicates with the port C (A-C) or a state where the port B communicates with the port C (B-C). Further, the solenoid valve 401 is controlled to be in a closed state.

By repeating the steps 2 to 9 described above, a thermal cycle can be applied to the sample 50 by continuously moving the sample 50 reciprocally between the low temperature region 38 and the high temperature region 36.

Also in the reaction processing apparatus 400 according to the present embodiment, since only one pump is used, the control of the movement of the sample can be easily performed, and the cost can be reduced.

Described above is an explanation based on the embodiments of the present invention. These embodiments are intended to be illustrative only, and it will be obvious to those skilled in the art that various modifications to constituting elements and processes could be developed and that such modifications are also within the scope of the present invention.

INDUSTRIAL APPLICABILITY

The present invention is applicable to a polymerase chain reaction (PCR).

Sequence number 1: forward PCR primer
Sequence number 2: reverse PCR primer
Sequence number 3: Probe
[Sequence Listing] NSG-70057W0 Sequence Listing.txt

What is claimed is:
1. A reaction processing apparatus comprising:
a reaction processing vessel including a channel in which a sample moves and a pair composed of a first air communication port and a second air communication port that are provided at respective ends of the channel;
a first heater in thermal contact with the channel;
a second heater in thermal contact with the channel;
a temperature control system connected to and configured to control the first heater to heat a first temperature region to a first temperature and the second heater to heat a second temperature region to a second temperature higher than the first temperature, the first temperature region and the second temperature region are disposed along the channel between the first air communication port and the second air communication port; and
a liquid feeding system configured to move and stop the sample in the channel,
wherein the liquid feeding system includes:
a single pump having a discharge port configured to discharge air;
a first air channel that connects the discharge port of the single pump and the first air communication port of the reaction processing vessel;
a second air channel that connects the discharge port of the single pump and the second air communication port of the reaction processing vessel;
a first switching valve that is arranged in the first air channel and is configured to switch between a state in which the first air communication port communicates

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 1
ggataatttg tttgcagttg atgtc                                          25

<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 2
caaatcctgt cacatataaa ttatttcgt                                      29

<210> SEQ ID NO 3
<211> LENGTH: 31
<212> TYPE: DNA
<213> ORGANISM: Artificial Sequence
<220> FEATURE:
<223> OTHER INFORMATION: Synthetic oligonucleotide probe

<400> SEQUENCE: 3
ccgtagatta ttaaaccgcc cttcctctgg a                                   31
``` with the discharge port and a state in which the first air communication port is opened to atmospheric pressure;

a second switching valve that is arranged in the second air channel and is configured to switch between a state in which the second air communication port communicates with the discharge port and a state in which the second air communication port is opened to the atmospheric pressure; and a control unit operatively connected to the pump, the first switching valve and the second switching value and configured to operatively control the single pump, the first switching valve, and the second switching valve.

2. The reaction processing apparatus according to claim 1, wherein the first temperature region is located on a first air communication port side and the second temperature region is located on a second air communication port side, wherein the control unit is configured to:

discharge air from the single pump and change the first switching valve to be in the state in which the first air communication port communicates with the discharge port and the second switching valve to be in the state in which the second air communication port is opened to the atmospheric pressure, to move a sample from the first temperature region to the second temperature region; and discharge air from the single pump and change the first switching valve to be in the state in which the first air communication port is opened to the atmospheric pressure and the second switching valve to be in the state in which the second air communication port communicates with the discharge port, to move the sample from the second temperature region to the first temperature region.

3. The reaction processing apparatus according to claim 1, wherein the control unit is configured to stop the discharging of the air from the single pump to stop the sample inside the channel.

4. The reaction processing apparatus according to claim 1, wherein pressure on a primary side and pressure on a secondary side become equal in the single pump when the single pump is stopped, and wherein the control unit is configured to change the first switching valve to be in the state in which the first air communication port is opened to the atmospheric pressure and the second switching valve to be in the state in which the second air communication port is opened to the atmospheric pressure to stop the sample inside the channel.

5. The reaction processing apparatus according to claim 1, wherein the first switching valve and the second switching valve are three-way valves.

6. A reaction processing system comprising:

a reaction processing vessel including a channel in which a sample moves and a pair composed of a first air communication port and a second air communication port that are provided at respective ends of the channel; and a reaction processing apparatus comprising:

a first heater in thermal contact with the channel;

a second heater in thermal contact with the channel;

a temperature control system connected to and configured to control the first heater to heat a first temperature region to a first temperature and the second heater to heat a second temperature region to a second temperature higher than the first temperature, the first temperature region and the second temperature region are disposed along the channel between the first air communication port and the second air communication port; and a liquid feeding system configured to move and stop the sample in the channel, wherein the liquid feeding system includes:

a pressurizing chamber that has an internal pressure maintained to be higher than atmospheric pressure in a surrounding environment of the reaction processing apparatus;

a single pump having a discharge port that is arranged inside the pressurizing chamber and is configured to discharge air from the discharge port;

a first air channel that connects the discharge port of the single pump and the first air communication port of the reaction processing vessel;

a second air channel that connects the discharge port of the single pump and the second air communication port of the reaction processing vessel;

a first switching valve that is arranged in the first air channel and configured to switch between a state in which the first air communication port communicates with the discharge port and a state in which the first air communication port is opened to an internal space of the pressurizing chamber;

a second switching valve that is arranged in the second air channel and is configured to switch between a state in which the second air communication port communicates with the discharge port and a state in which the second air communication port is opened to the internal space of the pressurizing chamber; and a control unit operatively connected to the pump, the first switching valve and the second switching value and configured to operatively control the single pump, the first switching valve, and the second switching valve.

7. The reaction processing system according to claim 6, wherein the first temperature region is located on a first air communication port side and the second temperature region is located on a second air communication port side, wherein the control unit is configured to:

discharge air from the single pump and change the first switching valve to be in the state in which the first air communication port communicates with the discharge port and the second switching valve to be in the state in which the second air communication port is opened to the internal space of the pressurizing chamber, when a sample is moved from the first temperature region to the second temperature region; and discharge air from the single pump and change the first switching valve to be in the state in which the first air communication port is opened to the internal space of the pressurizing chamber and the second switching valve to be in the state in which the second air communication port communicates with the discharge port, when the sample is moved from the second temperature region to the first temperature region.

8. The reaction processing system according to claim 6, wherein the control unit is configured to stop the discharging of the air from the single pump to stop the sample inside the channel.

9. The reaction processing system according to claim 6, wherein pressure on a primary side and pressure on a secondary side become equal in the single pump when the single pump is stopped, and wherein the control unit is configure to change the first switching valve to be in the state in which the first air communication port is opened to the internal space of the pressurizing chamber and the second switching valve to be in the state in which the second air communication port is opened to the internal space of the pressurizing chamber to stop the sample inside the channel.

10. The reaction processing system according to claim 6, wherein the first switching valve and the second switching valve are three-way valves.

* * * * *